United States Patent
Seegert et al.

(10) Patent No.: US 7,666,192 B2
(45) Date of Patent: Feb. 23, 2010

(54) SKIN GRAFTING DEVICES AND METHODS

(75) Inventors: Charles Seegert, San Antonio, TX (US); Royce W. Johnson, Universal City, TX (US); A. David Boccuti, Arlington, MA (US); Andrew Nicholas Gentile, Allston, MA (US); Sy Griffey, Fiar Oaks Ranch, TX (US); Teryl Blane Sanders, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 665 days.

(21) Appl. No.: 11/093,740

(22) Filed: Mar. 30, 2005

(65) Prior Publication Data

US 2005/0234485 A1   Oct. 20, 2005

Related U.S. Application Data

(63) Continuation-in-part of application No. 10/075,743, filed on Feb. 14, 2002, now Pat. No. 7,070,584, and a continuation-in-part of application No. 10/379,342, filed on Mar. 3, 2003.

(60) Provisional application No. 60/587,708, filed on Jul. 14, 2004, provisional application No. 60/629,001, filed on Nov. 18, 2004, provisional application No. 60/269,657, filed on Feb. 16, 2001.

(51) Int. Cl.
*A61B 17/50* (2006.01)

(52) U.S. Cl. .................................................. 606/131
(58) Field of Classification Search ............. 606/131, 606/132, 166; 600/562, 569, 570; 30/43.7
See application file for complete search history.

(56) References Cited

U.S. PATENT DOCUMENTS

| | | | | | |
|---|---|---|---|---|---|
| 1,391,635 | A | * | 9/1921 | Henry | 30/215 |
| 2,400,336 | A | * | 5/1946 | Bishop | 606/132 |
| 3,412,732 | A | * | 11/1968 | Simon | 606/132 |
| 3,583,403 | A | * | 6/1971 | Pohl et al. | 606/132 |
| 3,797,505 | A | * | 3/1974 | Gilhaus et al. | 132/76.4 |
| 5,578,662 | A | | 11/1996 | Bennett et al. | |
| RE35,421 | E | * | 1/1997 | Ruiz et al. | 606/166 |
| 5,795,584 | A | | 8/1998 | Totakura et al. | |
| 5,902,874 | A | | 5/1999 | Roby et al. | |
| 5,902,875 | A | | 5/1999 | Roby et al. | |
| 5,914,387 | A | | 6/1999 | Roby et al. | |
| 5,951,295 | A | | 9/1999 | Lyles et al. | |
| 5,997,568 | A | | 12/1999 | Liu | |

FOREIGN PATENT DOCUMENTS

WO   WO 96/05873   2/1996

\* cited by examiner

*Primary Examiner*—(Jackie) Tan-Uyen T Ho
*Assistant Examiner*—Gregory Anderson

(57) ABSTRACT

The present invention provides skin grafting and devices that comprise a systematic approach to the process of skin grafting, i.e., harvesting, post-excision processing and application of donor skin and pre and post-graft treatment of the recipient site.

21 Claims, 22 Drawing Sheets

SKIN GRAFTING DEVICES AND METHODS

CROSS REFERENCE

This application claims priority to U.S. Provisional Application Ser. No. 60/587,708, filed 14 Jul. 2004, and to U.S. Provisional Application Ser. No. 60/629,001 filed 18 Nov. 2004. This application is also a continuation-in-part of U.S. patent application Ser. No. 10/075,743 filed 14 Feb. 2002 now U.S. Pat. No. 7,070,584 that claims the benefit of U.S. Provisional Application Ser. No. 60/269,657, filed 16 Feb. 2001, and a continuation-in-part of co-pending U.S. patent application Ser. No. 10/379,342 filed 3 Mar. 2003.

BACKGROUND OF THE INVENTION

1. Field of the Invention

The present invention relates generally to skin grafting and related devices and methods. The present invention provides a systematic approach to the process of skin grafting, i.e., harvesting, post-excision processing and application of donor skin and treatment of the graft recipient site.

2. Description of the Related Art

Advances in medical technology have provided many patients with benefits inconceivable a century ago. In particular, skin grafting has enabled doctors to heal wounds with the patient's own skin from a harvest site on the patient. The skin grafting techniques have many wonderful benefits, but are still replete with a number of problems.

The process of split-thickness skin grafting can be envisaged as a series of steps; (1) harvesting the split-thickness-skin graft ("STSG") at a donor site; (2) processing of excised STSG; (3) application of the processed skin to the wound site; and (4) pre- and/or post-graft treatment to accelerate healing of the wound site. Each of these steps interposes various challenges and obstacles, e.g., technical, therapeutic and financial, in executing a successful graft.

In regard to the first step, harvesting a STSG at a donor site has traditionally been accomplished using powered, hand-held dermatomes. These devices are expensive and the operation is known to be highly dependent on user skill and training, and requires involved procedures to accurately obtain a successful harvest. These devices must be operated at a precise constant angle relative to the skin, with the exact amount of pressure to insure a uniform harvest. Slight variations in operative use of these dermatomes result in excised skin of variable-thickness, which sometimes must be discarded altogether. As a result, these devices are primarily wielded only by experienced plastic surgeons. Use of these dermatomes are generally confided to the operating room setting, increasing the cost of the procedure, especially given the average fee for operating room use.

There is a current need for harvesting procedures that require a lower degree of operator skill and are capable of being performed outside of an operating room, thus decreasing the costs of the procedure.

In regard to the second step of processing excised skin, it is highly desirable to maximize the coverage of the donor skin at the wound site for any given area of a potential donor site. Apart from minimizing trauma incurred at the donor site, a major factor limiting survival following extensive injury is insufficient availability of donor sites to provide enough skin for the required grafting procedures. One procedure is to mesh the skin graft i.e., creating slits in the excised donor skin to allow for the skin to be stretched. A graft-meshing machine is commonly used in hospital-based surgical practices, and generally allow for an expansion ratio of 3:1 to 9:1. The excised harvested skin is placed on a specific template, depending on the expansion ratio desired, and the template and graft are pressed through the mesher. While greater ratios than 9:1 may be possible using meshing techniques, there is a concomitant significant delay in epithelization with using such ratios. When healed, a meshed grafted site characteristically has a permanent "crocodile skin" or "weaved" appearance.

Micro grafting techniques, in which the donor tissue is actually minced in order to achieve a greater than 10:1 expansion ratio, are known in the art. Such techniques allow for a greater coverage area from a small donor site than meshing techniques. Traditional micrograft techniques, dating back to 1963, utilized minced skin that is between ⅛th inch (approximately 3 mm, or 3000 μm) and ¹⁄₁₆th inch (approximately 1.5 nm, or 1500 μm) in size. However, disadvantages of using pieces larger than 1500 μm have been noted. For example, in skin pieces of this size cells remote from a cut edge have a limited availability to migrate and proliferate and thereby contribute to forming new skin. In addition, the techniques employed have required each piece to be oriented epidermis upwards, making the procedure tedious and impractical. Further, the appearance of the new skin that is produced using particles of this size is poor, often having a cobblestone appearance.

There is currently a need for a procedure capable of producing micrograft particles in a size less than 1500 μm in a rapid and efficient manner, with a minimum of handling procedures, while resulting in skin pieces that are viable and capable of "taking" when applied to a wound site. Such technique would significantly aid in the ease and speed of operations utilizing micrografts.

The third step of the graft procedure, application of processed excised skin to the wound site, it is particularly relevant to the application of micrograft particles to a wound site. The effect of a decrease in size on micrograft particles on the inter-particle distance for a given expansion ratio is shown in schematic form in FIG. 27. Given that the epitheliaztion of the inter-particle wound surface is affected by migration and proliferation of keratinocytes from the micrografts, it is readily evident that the most effective distribution is that idealized in FIG. 27. Current methods of distributing micrografts, such as mechanical spreading results in clumps or aggregates of skin particles, frustrating an even distribution. In addition, in larger aggregates, some micrograft particles will not be in direct contact with the wound bed. Such particles cannot readily integrate with the wound bed and also will have a reduced potential for nourishment from the wound fluid exudates and consequently have an decreased potential to remain viable. Thus, the aggregation of micrografts reduces the efficiency of epithelization and may significantly increase the time required to close a wound.

There is a current need for devices and methods to effect an even distribution of micrcograft particles on a wound surface, thereby promoting the efficiency of epithelization.

The fourth step of the graft procedure relates to pre- and/or post-graft treatment to accelerate healing of the wound site. As is known in the art, closure of surface wounds involves the inward migration of epithelial, dermal and subcutaneous tissue adjacent to the wound. This migration is ordinarily assisted through the inflammatory process, whereby blood flow is increased and various functional cell types are activated. Through the inflammatory process, blood flow through damaged or broken vessels is stopped by capillary level occlusion; thereafter, cleanup and rebuilding operations may begin.

When applied over a sufficient area of the wound, negative pressures have been found to promote the migration toward the wound of surrounding cutaneous and subcutaneous tissues. In practice, the application to a wound of negative gauge pressure, commercialized by Assignee or its parent under the designation "Vacuum Assisted Closure" (or "V.A.C.®") therapy, typically involves the mechanical-like contraction of the wound with simultaneous removal of excess fluid. In this manner, V.A.C.® therapy augments the body's natural inflammatory process while alleviating many of the known intrinsic side effects, such as the production of edema caused by increased blood flow absent the necessary vascular structure for proper venous return.

Despite being highly successful in the promotion of wound closure and healing many wounds previously thought largely untreatable, some challenges remain with the use of negative pressure therapy. One such area is in the frequent changing of the wound dressing. As the wound closes, binding of cellular tissue to the wound dressing may occur and use of traditional V.A.C.® therapy necessitates regular changing of the dressing. If cellular tissue has grown excessively into the dressing, there is the potential that dressing changes without due care and attention may result in some tissue damage at the wound site. The problem of frequent dressing changes would likewise tend to frustrate the combination of micrografts with negative pressure treatment, in that the dressing change may remove or displace micrografts.

There is current need for methodologies to address the challenges involved with frequent dressing changes and to effectively combine the micrograft techniques with negative pressure treatment to effect enhancement of wound closure.

SUMMARY OF THE INVENTION

Devices and methods are provided for enhancing the ease, speed and reproducibility of harvesting, processing, and applying skin particles prepared from STSG, and further wherein such application may be combined with negative pressure therapy. The term "wound" as used in the context of the present invention, may include, but is not limited to, burns, incisional wounds, excisional wounds, ulcers, traumatic wounds, and chronic open wounds.

Skin Harvesting

One aspect of the present invention is a skin-harvesting device that is comparatively easily operable compared to hand held dermatomes and that removes a sufficient amount of skin at a substantially consistent thickness and dimension during use.

In some embodiments of this aspect of the invention, a skin-harvesting device comprises a base having a base plate that has a proximal end, a distal end, and two side ends, and defines a window adjacent to the proximal end that is adapted to be pressed against a harvest site to allow skin to protrude through. In embodiments wherein the base plate is a generally rectangular base plate, the proximal and distal ends form lateral ends and the side ends form longitudinal ends.

In some embodiments, slide tracks are disposed along the side ends of the base and adapted to couple with slides are positioned at outside lateral ends of a cutting frame that includes a blade housing adapted to house a blade at a predetermined angle, and a motor adapted to oscillate the blade. In some embodiments, the blade is aligned traverse to the side ends and generally parallel to the proximal end and the predetermined angle forms an oblique angle relative to the proximal end. An adjustable thickness plate is connected to the cutting frame at a forward end and adapted to raise or lower, wherein the adjustable thickness plate is adapted to contact skin protruding through the window and uniformly even out the surface thereof prior to cutting by the blade. In some embodiments, the adjustable thickness plate comprises a flat plate parallel with and substantially co-extensive with the window defined by the base plate. In some embodiments, this flat plate is made of a transparent material, which may be plastic.

In some embodiments, the angle of the blade in the blade housing is adapted to be fixed relative to the window to eliminate any variation in tissue harvesting caused by changes in the blade angle. In typical embodiments, the device is adapted to be disposable after a predetermined number of uses. In some embodiments, batteries are provided to power the motor, and the device is adapted to be used on a single patient (single patient use). In further embodiments, the cutting frame is adapted to move freely along the tracks of the base dependent on directional changes by the user.

Embodiments of this aspect of the invention also include a skin-harvesting device with a motor having an axle coupled through the cutting frame to the blade and adapted to oscillate the blade, a power source connected to the motor, which may comprises a battery pack connected to the motor. Embodiments include an ergonomic cover housing the cutting frame and motor, the ergonomic cover defining a skin-graft retrieval area to allow a user access to any skin collected after harvesting. Internal or external slide rails formed at side ends of the base and track fixtures may be positioned on lateral ends of the cutting frame, the track fixtures being adapted to slide in the corresponding internal or external slide rails of the base and thereby translate the cutting frame along the base. The blade may be coupled to the blade housing by any suitable method including via thermoplastic welding or via fasteners. In some embodiments tab portions are positioned along the proximal end of the base adjacent the window and/or grips are positioned on the base to provide a user an area to apply pressure to the base during use of the device. In some embodiments, the base has an open end to allow the cutting frame to be removed from or placed within the base. In other embodiments, there are a plurality of ridges formed on the skin-facing surface of the adjustable thickness plate, the plurality of ridges being adapted during use to grip the skin prior to incision and/or a plurality of ridges formed on the skin-facing surface of the base adjacent the window adapted to grip the skin adjacent the base window.

Embodiments include having at least one fastener coupled through the cutting frame to the adjustable depth plate adapted to raise and lower the adjustable depth plate. A skin-depth wheel or a skin-depth slide may be positioned on the cover and coupled to the adjustable thickness plate to raise or lower the adjustable thickness plate with respect to the skin. Indicia may be printed on the cover adjacent the skin-depth wheel or skin-depth slide to indicate the depth of the adjustable thickness plate when the skin-depth wheel is rotated or the skin-depth slide is moved. Some embodiments include a roller wheel positioned before the blade and blade holder and rotating about an axle coupled to the cover, wherein said roller wheel comprises a plurality of teeth about the perimeter of the wheel adapted to puncture or hook the skin prior to incision by the blade adapted to secure the skin during use onto the roller wheel after severance.

One embodiment includes a base plate defining a base window at a forward end thereof and having slide rails positioned at lateral internal edges of the base plate; a frame base adapted to slide in the slide rails of the base plate; a frame connected to the frame base; a plurality of slides coupled along lateral edges of the frame and adapted to engage the slide rails and slide freely; base grips positioned along lateral ends of the base plate and adapted to support pressure from a user thereon; an ergonomic cover adapted to encompass the frame and frame base and defining a cover window at a forward end; cover grips positioned at lateral edges of the cover adapted to allow a user to firmly grip the cover and apply pressure during use of the device; a motor coupled to the frame; a power source connected to the motor; a blade holder coupled to a forward section of the frame via a guide pin; a blade coupled to the blade holder at a predetermined angle; an adjustable depth plate coupled to the frame adjacent and forward from the blade holder; a cam connected to the adjustable depth plate having a cam dial adapted to control the raising and lowering of the adjustable depth plate with respect to the base window; wherein the device is adapted to be pressed against tissue to allow a uniform surface of tissue substantially parallel to the base to protrude through the base window, wherein the adjustable depth plate is adapted to press the tissue to facilitate uniformity in thickness of any tissue cut by the blade, and wherein the blade is adapted to sever the tissue and deposit the tissue thereon for collection by a user.

Another embodiment includes: a base defining a base window adapted during use to be pressed against skin to allow the skin to protrude through and to see the skin prior and during incision; a cover housing a cutting blade, motor connected to the cutting blade, and a power source connected to the motor, the cover being adapted to translate along the base; the cover defining a skin-graft retrieval area adjacent the cutting blade, which during use supports skin severed by the cutting blade and provides access to the severed skin; an adjustable depth plate positioned forward of the cutting blade and housed within the cover; a skin-depth wheel or a skin-depth slider positioned on the cover adjacent the skin-graft retrieval area adapted to provide manual control during use of the adjustable depth plate; and a switch positioned on the top of the cover for activation and de-activation of the motor. A handle-portion having a power switch may be positioned on an underside thereof, wherein said handle-portion is adapted to be gripped by a user during translation of the cover along the base during use of the device. A radius portion may surround the perimeter of the base adapted to provide an area for a user to assist in applying pressure to the device. In some embodiments, the cover defines at least one depression adapted to conform to a user's hand for secure gripping and movement when the cover is translated along the base. In some embodiments, there is a plurality of ridges formed on the cover in the skin-graft retrieval area to support severed skin and/or there are textured ridges positioned on lateral edges of the cover for a user to grip the cover and apply a pressure on the cover to translate the cover along the base, said base having an extended area adjacent the window on opposing sides for a user to apply pressure to the base during use of the device, wherein there are optionally a pair of raised portions on the extended area of the base for a user to apply pressure to the base during use of the device. In some embodiments, base may further comprise an enlarged portion or tabs adjacent the window on opposing sides for a user to apply pressure to the base during use of the device. There may be external tracks positioned along lateral edges of the base. In some embodiments, there is an open end to allow the user to extract the cover from the base. Also, the cover housing a cutting blade may be tubular.

This aspect of the invention also provides for methods of harvesting skin samples by use of the devices described above. Some embodiments comprise contacting skin from a harvest site, also called a donor site, applying pressure to the base of the device such the skin protrudes through the window in the base plate of the device, adjusting the thickness plate of the device such that the skin forms a uniform surface substantially parallel to the base, then frame coupled to the blade to sever the protruding skin such a section of split-thickness skin is produced, then collecting the skin section.

These features described above together eliminate the main components of user variability and thus allow a uniform split thickness graft to be obtained by less skilled and less experiences users than known in the art. Alignment with a mincing device is also included, to allow the graft to be processed into small particle sizes.

Tissue Processing

A second aspect of the present invention provides a tissue processor for the expedient preparation of micrograft skin particles suitable for grafting. In some embodiments, a tissue processor according to this aspect of the invention may be used in combination with the skin-harvesting device of the preceding aspect of the present invention.

In regard to current invention, the cutting edges and the blades of the skin processor form a defined area in the cutting plane, whether the defined area is formed in one step or two sequential steps requiring the blades and excised skin to be rotated 90° relative to each other, as further described below. Skin pieces produced by such a cutting process may decrease in size relative to that area defined in the cutting plane by the blades, due at least in part by the combination of the inherent elasticity of skin and the degree that the originating excised skin was stretched on a cutting support. Consequently, for the purposes of the instant disclosure, the size of skin pieces is given in reference to that defined area in the cutting plane made by the cutting blades. Further in this regard, skin pieces described by a one dimensional term of measurement, e.g., 600 µm, refer to skin pieces resulting from a tissue processor such that the area defined by the blades in the cutting plane is a substantially square shape with sides of 600 µm. E.g., in a process whereupon a STSG is cut once by a stack of parallel blades, then turned 90° for a second cut, and the parallel blades are set apart at a distance of 600 µm, the resulting skin pieces may be termed "600 µm (or micron) skin pieces," "600 µm micrografts," or "600 µm nanografts," In that the skin pieces of the current invention are not limited by shape, i.e., are not necessarily substantially square, skin pieces are also alternatively defined by that two-dimensional area defined by the blades in the cutting plane. E.g., a substantially square skin piece of "about 600 µm" is included in those skin pieces represented by the term of "about 360000 µm$^2$," but as the latter term is only limited by that area it encompasses skin pieces of all shapes as defined by the blades in the cutting plane, e.g., a circle with a diameter that approximates to 677 µm.

In regard to the term "micrograft," for the purposes of the instant disclosure this term generally applies to minced skin pieces of less than about 5 mm in size (assuming a substantially square shape) or 25 cm$^2$ in area, and is used interchangeably with the term "minced skin pieces." The term "nanograft," for the purposes of the present invention, means skin in the range of about 250 to about 1000 µm or in the range of about 60,000 µm$^2$ to about 1 mm$^2$, as defined above. In some embodiments, the nanografts are substantially uniform. In some embodiments, nanografts may be prepared in the size of about 300, or about 400, or about 500, or about 600, or about 700, or about 800, or about 900 µm. In preferred embodiments, nanografts are prepared in the size of about 500, about 600 or about 700 µm. Nanografts may also be prepared in the size of about 90,000, or about 160,000 or about 250,000, or about 360,000, or about 500,000 or about 650,000, or about 800,000 µm$^2$. In preferred embodiments, the nanografts are prepared in the size of about 250,000, or about 360,000, or about 500,000 μm². In regard to the present invention, the term "substantially square" in relation to a skin piece means that the skin piece is the product of a shape formed in the cutting plane of the blades producing the skin piece, wherein that shape that is substantially square. In regard to the present invention, the term "substantially uniform" in relation to skin pieces means that the skin pieces are the product of shapes formed in the cutting plane of the blades producing the skin pieces, wherein such shapes are substantially uniform in shape and size.

In reference to FIG. 27 and the schematic describing the concept of the enhancement ratio, it will be evident that nanografts of a substantially uniform size will aid the reproducibility of desired effectiveness of the nanograft particles at a defined enhancement ratio, and if dispersed relatively evenly, the uniform size will aid a uniform pattern of outgrowth and aid in the cosmesis of the resulting graft. In the latter case this aspect of the invention is achieved combined with that of the subsequent aspect described infra.

In one embodiment, a tissue processor consists of a series of sharpened blades arranged parallel to one another, and maneuvered such as to cut the STSG in two passes, wherein the second pass is at a ninety degree angle to the first pass.

In one embodiment, a device for cutting skin comprises a plurality of circular blades aligned in parallel on a blade shaft; a screen comprising a dorsal and a ventral surface, a leading edge and a trailing edge, and plurality of parallel transverse slits disposed in the screen such that the slits align with the parallel blades and wherein the blade shaft is located on the screen dorsal surface side and the circular blades protrude through the slits such that each blade protrudes a distance from the screen's ventral surface, which in some embodiments is an equal distance from the screen's ventral surface. In some embodiments, that portion of the screen proximal to the trailing edge is displaced by a step portion generally towards that side on which the blade shaft is located, i.e., the screen dorsal surface side, and where the step is parallel to the trailing edge and is located between the trailing edge and the protruding blades. In such embodiments, the step portion effects the extrusion of cut skin pieces when, during use, a STSG graft supported on a cutting mat is translated along the ventral surface of the screen in the direction from the leading edge to the trailing edge, and the cut skin pieces generally remain in contact with the cutting mat. In some embodiments, the step is a generally right angle shape or is a generally arc shape. In some embodiments the circular blades are rotatably disposed on the blade shaft. In some embodiments, the device may also have a plurality of spacers aligned on the blade shaft with one or more spacers located between each of the plurality of circular blades. In some embodiments, the leading and the trailing screen edges are on a generally horizontal plane, and the screen from the leading edge describes a plane at a descending angle, and returns to a generally horizontal plane, or a plane at a slight increase, in the general location of the line described by the trailing edge side of the minor arcs described by the protruding blades, and wherein the step portion returns the trailing edge to a generally horizontal plane relative to the leading edge.

Other embodiments encompass a skin processing device that comprises: a generally rectangular base wherein the proximal end is adapted to couple with the above described device for cutting skin, where the blade shaft is placed lateral relative to the base; a sled and a removable cutting mat support surface adapted to be placed on the sled where, during use, the sled is adapted to translate longitudinally along the base, and wherein the circular blades and the cutting mat on the sled are positioned relative to each other such that during use a STSG placed on the cutting mat is cut into pieces. In some embodiments, the skin processing device further comprises a handle adapted to translate the sled along the base.

In some embodiments, the parallel circular blades aligned on the blade shaft are adapted to couple to the base such that during use they are yieldably biased, i.e. moved, in a plane perpendicular from the base by the translation of the sled with the cutting mat to such an extent that a predetermined force is exerted on the cutting mat by the circular blades. In some embodiments, predetermined force is determined by a resistance means, which may be a compression spring, which may be a helical compression spring.

In some embodiments, the blade shaft and screen are covered by and are adapted to couple to the base by a detachable housing. In typical embodiments, the housing has a generally rectangular dorsal surface side, two lateral sides and a two longitudinal sides in a generally orthogonal relationship to one another and an open ventral side with two ventral lateral edges adapted to be detachable coupled to the longitudinal edges at the proximal end of the base, and a trailing ventral longitudinal edge and a leading ventral longitudinal edge. In some embodiments, both ventral longitudinal edges have recessed portions adapted to couple to the respective screen trailing and leading edges, wherein the ventral trailing longitudinal edge is adjacent to the proximal end of the base and the leading longitudinal ventral edge faces the direction from which the sled translates along the base when in use to effect the cutting of the STSG. In typical embodiments, the recessed portions of the ventral longitudinal edges with the coupled screen are disposed to allow for the translation along the base of the sled such that the cutting mat contacts the circular blades protruding through the screen. In some embodiments, the ends of the blade shaft are adapted to be movably coupled to interior surfaces of the lateral sides of the housing such that during use the blade shaft can be yieldably biased in the plane perpendicular to the base.

In some embodiments the predetermined force is determined by the maximum operative compression of a plurality of helical compression springs that, during use, are adapted to exert increased force on the blade shaft when the blade shaft is yieldably biased during use by the contact of the circular blades with the cutting mat during translation of the sled, wherein the increased force is exerted proximal to both ends of the blade shaft, i.e., on both sides of the circular blades. In some embodiments, the helical compression springs are aligned on a plurality of bolts, with proximal ends and distal ends, aligned perpendicular to the base and the proximal ends of the bolts are adapted to contact the blade shaft and the blade shaft is positioned between the proximal end of the bolt and the base, and the distal ends of the bolts are adapted to contact the helical compression springs, which, during use, are adapted to be compressed against the dorsal surface side of the housing.

In some embodiments, the cutting mat has a hydrophilic surface and in some embodiments the cutting mat is comprised of a poly-ether block amide resin. The surface of the cutting mat may be textured, which texture may comprise pores in the range of 15 μm to 100 μm, or in the range of 30 to 75 μm deep, which may include depths of 32, 34, 36, 38, 40, or 42 μm deep.

The parallel blades may be adjustably spaced to result in nanograft particles as described above, i.e., in the range of about 250 to about 1000 μm or in the range of about 60,000 μm2 to about 1 mm2, as defined above. They may also be spaced apart at about 250, or about 300, or about 400, or about 500, or about 600, or about 700, or about 800, or about 900, or about 1000 μm.

In another embodiment, the skin processing device comprises a generally rectangular base wherein a proximal end is adapted to couple to a skin cutting device that comprises a plurality of circular blades aligned in parallel on a blade shaft aligned lateral relative to the base, a screen comprising a dorsal and a ventral surface, a leading edge and a trailing edge, with a plurality of parallel transverse slits, such that the parallel slits align with the parallel blades and the screen is adapted such that the blades are located on the screen dorsal surface side and protrude through the slits such that each blade protrudes an equal distance from the screen ventral surface, and a sled with a removable cutting mat skin support surface, wherein, during use, the sled and cutting mat are adapted to translate longitudinally along the base. Further, the circular blades and blade shaft may be adapted to couple to the base such that during use they are yieldably biased by the translation of the cutting mat until a predetermined force is exerted on the cutting mat by the circular blades.

Some embodiments encompass a cutting device comprising a plurality of blades aligned on a blade shaft, a screen with a plurality of slits disposed therein, wherein the slits are disposed such that they align with the blades that protrude through the slits disposed in the screen, a cutting mat adapted to translate along the surface of the screen wherein the blades protrude, such that during use the blades contact the cutting mat. In some embodiments, the blades are yieldably biased during use by contact with the cutting mat, wherein the blades are yieldably biased to an extent regulated by a predetermined force, wherein that force is determined by a resistance means.

Embodiments of the present invention also encompass methods wherein the aforementioned skin processing device comprising a skin cutting device is used to prepare nanografts. In such embodiments, a STSG, as may be suitably prepared as disclosed in the first aspect of the present invention, is placed on the cutting mat and cut into strips by one pass through the circular blades, the cutting mat is removed, turned 90°, and replaced on the sled and cut once more, thereby preparing substantially uniform nanografts. Such nanografts may be in the size range of about 500 µm to about 1000 µm. Nanografts of about 250 µm, or about 300 µm, or about 400 µm, or about 500 µm, or about 600 µm, or about 700 µm, or about 800 µm, or about 900, or about 1000 µm may also be prepared by varying the spacing between the circular blades of the skin cutting device.

In another embodiment, multiple sets of processors are arranged perpendicular to one another in a single tissue processor, such that the tissue is processed in one step by the use, and in which the tissues are cut to the appropriate size in one pass. In a third embodiment, a curved cutting surface may also be provided to ensure that even pressure is applied across the surface of the STSG so that uniform tissue particles are produced.

The present invention also provides for extrusion or extraction for removing the tissue samples from the tissue processor as the size range of the tissue processed may result in the processed tissue becoming trapped within the confines of the processor, such as between the parallel-arranged blades. One embodiment is the aforementioned use of a screen comprising a step portion that effects the extrusion from the blades of cut skin pieces. In another embodiment, an extractor consists of a series of wires interspersed between the blades, and positioned below the cutting surface of the blades. In typical embodiments, the wires are extended to a handle at their distal end, and hinged at their proximal end. After processing, the wires can be pulled from between the blades by the handle, which in turn grasps the processed tissue. In such embodiments, the processed tissue is then captured by the extractor for easy removal, such as by flushing the extractor, or wiping the extractor.

Application of Skin Particles

The third aspect of the present invention provides methods and devices to effect a substantially even distribution of micrograft particles. Embodiments of this aspect of the invention include methods for applying skin particles to a wound site, comprising the steps of providing minced skin particles suspended in an physiologically compatible gel or aqueous solution, depositing minced skin particles onto a transfer substrate, and applying the particle-side of the transfer substrate to a wound. Embodiments of this aspect of the invention also provide for devices for performing the aforementioned methods.

In some embodiments, a suspension of minced skin in a physiologically compatible aqueous solution is placed in a reservoir connected to a negative pressure source with a transfer substrate being between the suspension and the negative pressure source. In such embodiments, negative pressure is applied effecting the deposition of the minced skin particles onto on surface of the transfer substrate, which is subsequently removed for application to a wound. In another embodiment, a super-absorbent sponge or polymer transfer substrate is used to suck up the physiologically compatible suspension medium, leaving the micrograft particles deposited on the surface of the sponge. In other embodiments, the minced skin suspension in a physiologically compatible aqueous solution is poured through a drain box adapted to capture the skin particles. In typical embodiments, after draining a transfer substrate is applied to the drain box such that the captured minced skin particles are deposited onto the transfer substrate, whereupon the transfer substrate is removed for application to a wound. In some embodiments, the minced skin particles are captured in the drain box by hooks or by depressions.

In various embodiments, the transfer substrate is a polymer mesh, which may be included or absorbed by the wound. In some embodiments the transfer substrate is applied to the wound for a predetermined time. In some embodiments the physiologically compatible aqueous solution is saline, which may be phosphate buffered saline. In other embodiments, the transfer substrate is a fibrous growth enhancing matrix. In some embodiments, negative pressure therapy is applied to the wound site prior and/or subsequent to transfer of skin particles to the wound.

In further embodiments, the physiologically compatible gel is contained in a first reservoir and optionally the minced skin aqueous suspension is contained in a second reservoir, wherein the physiologically compatible gel reservoir and optional second minced skin aqueous suspension are fluidly connected to a dispenser that is adapted to deposit the gel and optionally the minced skin aqueous suspension on to a transfer substrate, which may comprise a mesh roll. In typical embodiments, the mesh roll is then applied to a wound with the side with skin particles in contact with the wound surface. In some embodiments, the mesh roll is disposed in roll form on a roll bracket coupled to the dispenser. In typical embodiments, the surface of the mesh roll with minced skin particles is adhered to the periphery of a wound and the dispenser with the coupled roll bracket is pulled across the wound, and the gel and optionally the minced skin aqueous suspension is extruded from the dispenser and deposited on the mesh roll as it is drawn from the roll bracket by the pulling motion and is applied to the wound. Embodiments also encompass further comprising skin particles in suspension in the physiologically compatible gel contained in the first reservoir.

In various embodiments, the transfer substrate is a polymer mesh, which may be included or absorbed by the wound. In other embodiments, the transfer substrate is a fibrous growth enhancing matrix. In some embodiments, negative pressure therapy is applied to the wound site prior and/or subsequent to transfer of skin particles to the wound.

Negative Pressure Therapy

A fourth aspect of the present invention provides the use of nanograft particles with negative pressure therapy. Embodiments encompass methods of treating a wound comprising applying skin nanograft particles to the wound, applying a pad adapted for use with nanograft particles shaped to conform a wound site, applying an air-tight seal removeably adhered to said pad, and applying a negative pressure source in fluid communication with said pad. In some embodiments the pad is comprised of bioabsorbable materials and in some embodiments the nanograft particles are applied to the wound in a bioabsorbable matrix. Other embodiments include applying a primary dressing over the nanograft particles, then applying a pad adapted for use with nanograft particles shaped to conform wound dressing. In some embodiments, a gel may be applied to the primary dressing before applying the pad, which may be an antibacterial gel. In some embodiments, the pad may be an open-cell reticulated porous foam.

In some embodiments, the skin nanograft particles are applied to the wound in a gel, which may be an antibacterial gel or a gel growth-enhancing matrix. In some embodiments a primary dressing may then be applied over the wound. In other embodiments, the nanograft particles are applied in a fibrous growth-enhancing matrix.

Embodiments also include a flexible tube communicating between the pad and the negative pressure source and a removable canister in fluid communication between the pad and the negative pressure source.

This aspect of the invention also includes wound dressings that are adapted for use of nanograft particles with negative pressure therapy. In some embodiments, the dressing comprises a gel, which may be an antimicrobial and/or antibacterial gel or a gel growth-enhancing matrix. In some embodiments, the dressing may comprises a fibrous growth-enhancing matrix, which may comprise bioabsorbable materials.

The aspects of the present invention may be used as an integrated systematic approach of applying skin grafts to a wound site, or one or more of the devices and/or methods of the present invention may be incorporated with other techniques. In regard to the comprehensive approach encompassed by the present invention, the invention also provides for kits comprising a skin harvesting device in accordance with the first aspect of the present disclosure and a skin processing device in accordance with the second aspect of the present disclosure, and instructions for use thereof. Embodiments include a kit further comprising one or more apparatus suitable for conducting the method disclosure in the third aspect of the present invention and instructions for use thereof. Additional embodiments include a kit further comprising a wound dressing suitable for applying nanografts to a wound site in combination with negative pressure therapy according to the fourth aspect of the present disclosure and instructions for use thereof.

BRIEF DESCRIPTION OF THE DRAWINGS

A more complete understanding of the method and apparatus of the present invention may be obtained by reference to the following Detailed Description of the Invention, with like reference numerals denoting like elements, when taken in conjunction with the accompanying Drawings wherein.

DETAILED DESCRIPTION OF THE INVENTION

A. Skin-Harvesting Device and Methods

The present invention obviates the requirement of prior skin-harvesting devices of a high-degree of user skill, the resulting ease of use thereby providing the potential for reduction in overall costs and expenses associated with operations that utilize such dermatomes.

Figure 1:
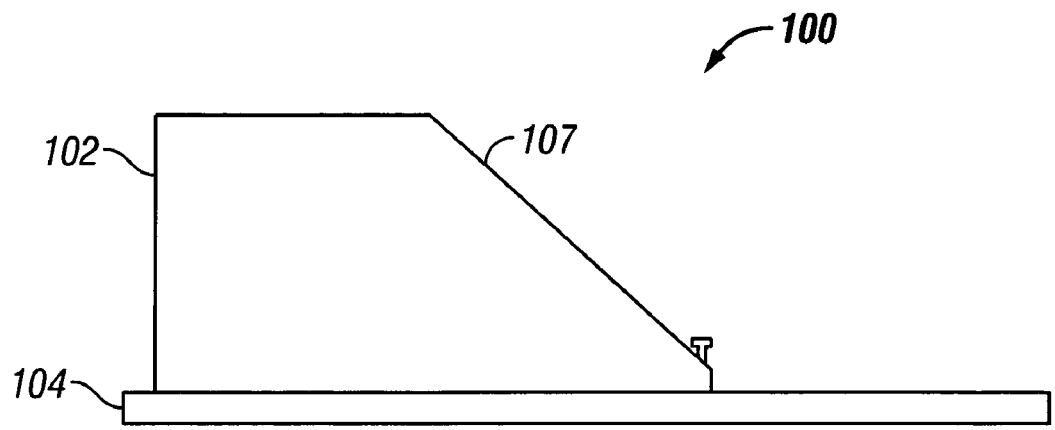
FIG. 1 is a side-plan view of a skin-harvesting device according to one embodiment of the first aspect of the present invention.
Figure 2:
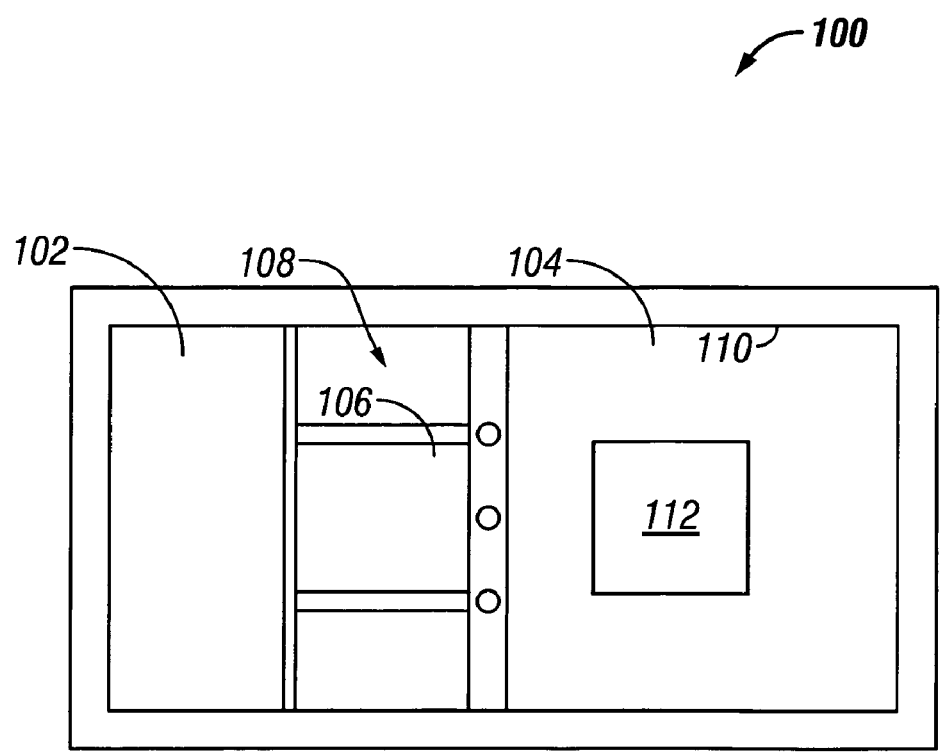
FIG. 2 is a top plan view of the skin-harvesting device of FIG. 1.

Referring first to FIGS. 1 and 2 in combination, there is shown side and top plan views of a skin-harvesting device 100 of the present invention in an exemplary first embodiment. The skin-harvesting device 100 includes a cutting frame 102 and a base 104 adapted to slideably receive the cutting frame 102 therein.

The cutting frame 102 is adapted to hold a cutting blade 106, such as a typical razor blade, therein. The cutting frame 104 is generally trapezoidal, including a sloped front portion 107 that provides access to an open area 108 for the user to see any amount of skin on the cutting blade 106, and to allow a user access to any skin harvested on the cutting blade 106 at any given time. The cutting frame 104 is specifically designed for secure gripping and manipulation during use of the skin-harvesting device 100.

The base 104 is generally rectangular, and includes slide rails 110 at the longitudinal ends of the base 104 adapted to receive track fixtures (not shown in these FIGS.) from the cutting frame 102 therein. A window 112 is provided at one end of the base portion 104. The base 104 is interchangeable with other bases having a larger or smaller window 112. The window 112, is specifically adapted to allow skin from the patient to protrude therethrough, and to allow a user to see the skin site from which the skin sample will be harvested. Although the window 112 preferably is large enough to allow about a 1 inch by about 1 inch square piece of tissue therethrough, other sized windows are contemplated to be within the scope of the present invention.

Figure 3A:
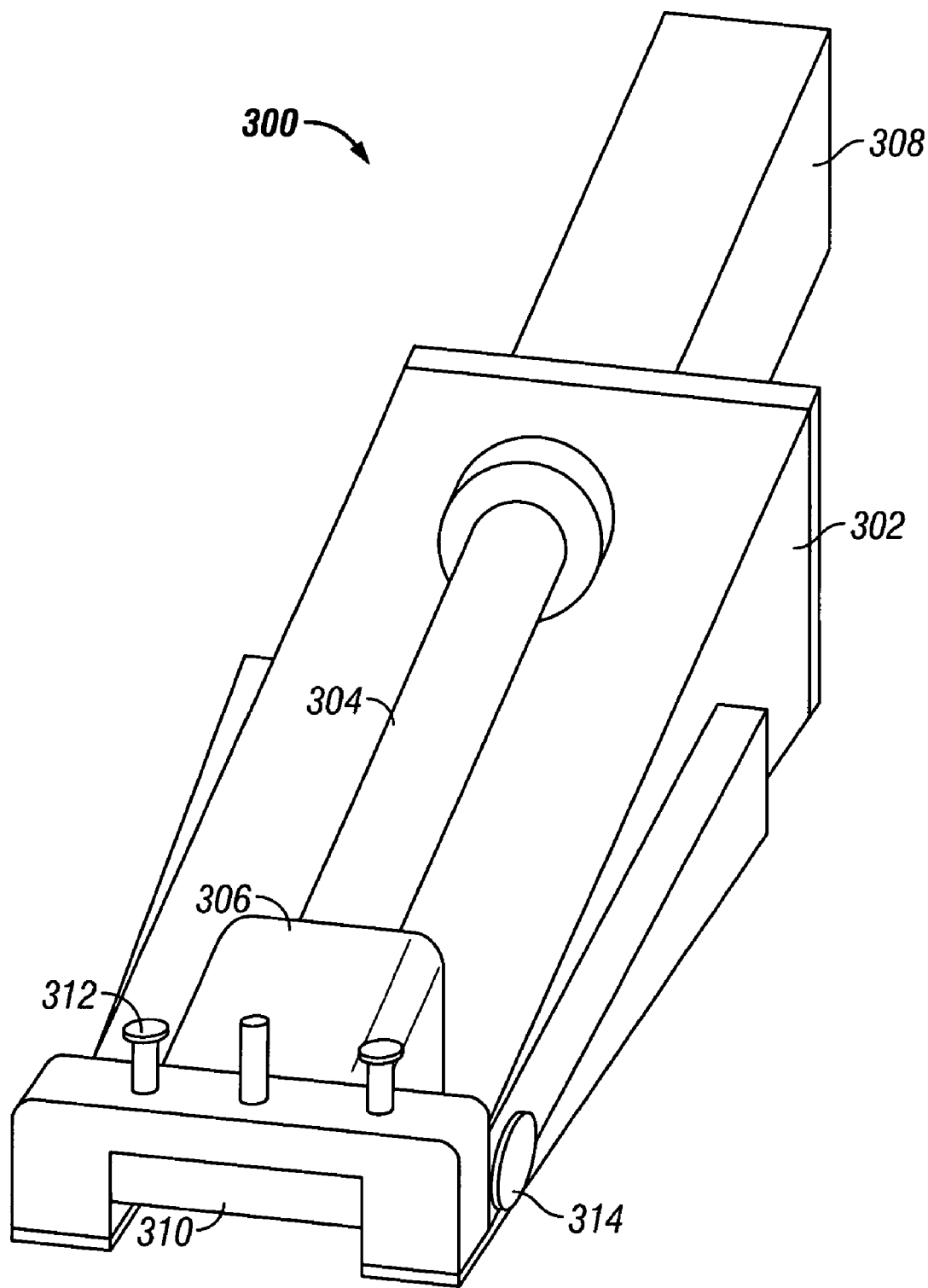
FIG. 3A is an isometric view of the cutting assembly of the skin-harvesting device of FIG. 1.

Referring now to FIG. 3A, an isometric view of the cutting assembly 300 of the skin-harvesting device 100 is shown. The cutting assembly 300 includes a blade frame 302 having a cutting blade 306 housed therein at a predetermined angle with respect to the bottom surface of the blade frame 302. The cutting blade 306 is connected to a motor shaft 304, which in turn is connected to a motor 308 outside of the cutting frame 302. The location of the motor 308 outside of the blade frame 302 prevents the motor 308 from being effected such as by fouling by debris, during use of the skin-harvesting device 100, and allows reuse thereof without cleaning, or with substantially reduced cleaning as compared to that of the blade frame 302.

Batteries or other power supplying apparatus are provided to power the motor 308. At a front end of the cutting assembly, centered and extending horizontally across the front end is provided an adjustable plate 310, which may be raised and lowered via fasteners 312, such as threaded screws, pins, and the like. It is appreciated that other adjustment devices may be suitably used without changing the scope of the present invention. The adjustable plate 310 controls the thickness of skin that protrudes through the window 112 (FIG. 2), and insures a consistently uniform thickness of skin is harvested during use.

Figure 3B:
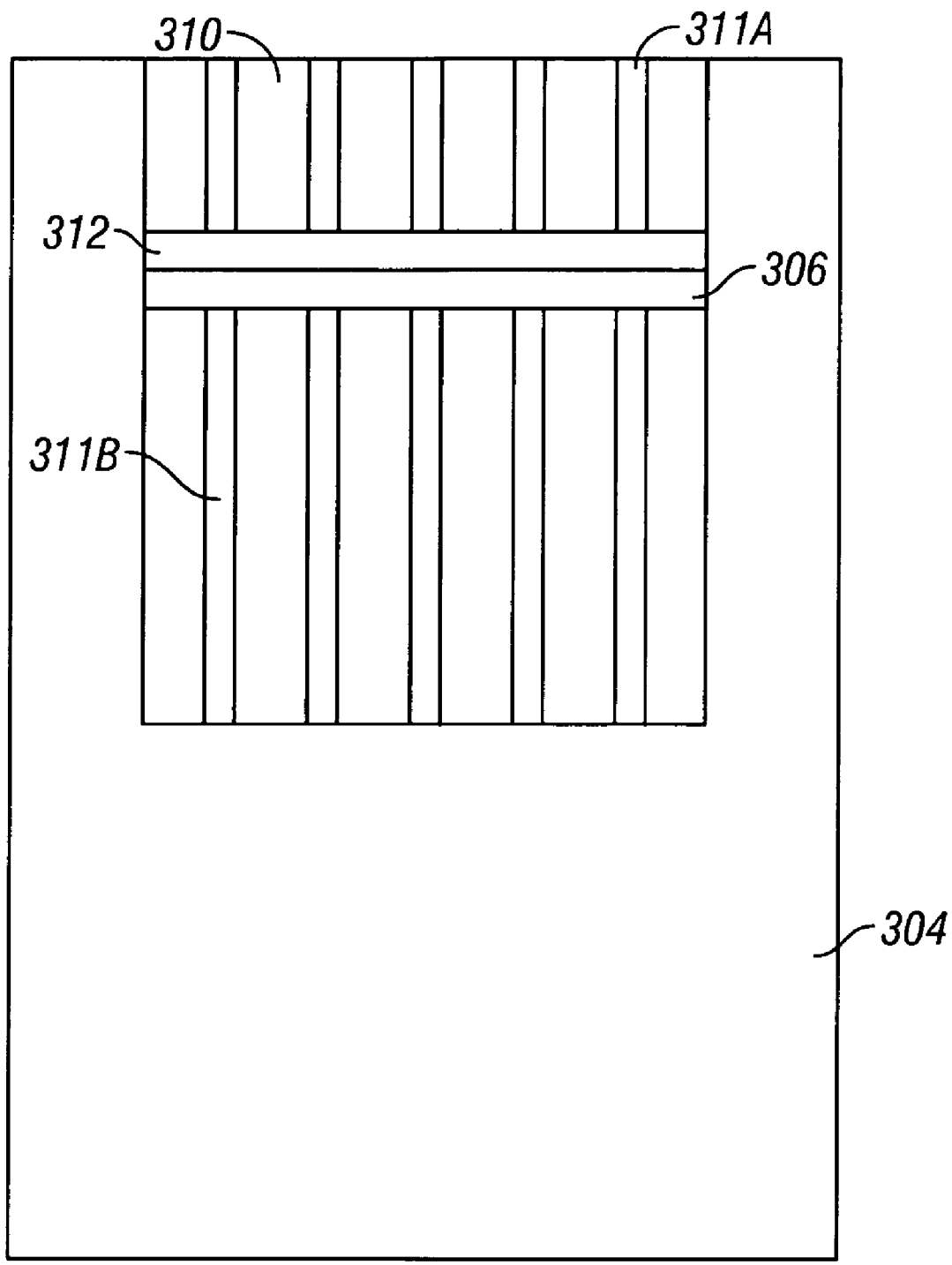
FIG. 3B is a bottom plan view of a base used in conjunction with the cutting assembly of FIG. 3A.

Referring to FIG. 3B, the bottom surface of a base 304 used in conjunction with the blade frame 302 (FIG. 3A). To firmly grip the skin during harvesting, the adjustable plate 310 may be provided with a plurality of ridges 311a, which are adapted to grip the skin and prevent any unnecessary movement of the skin during incision by the blade 306. Likewise, the base 304 may have a plurality of ridges 311b immediately adjacent the window 312 for similar purposes. As such, using an adjustable plate 310 with ridges 311a or a base 304 with ridges 311b alone or in combination provides sufficient friction to incise the skin accurately.

When actuated, the motor 308 (FIG. 3A) functions to laterally oscillate the cutting blade 306, which facilitates severing skin for harvesting. The cutting blade 306 may be replaced periodically, or the blade frame 302 may be discarded altogether after detachment from the motor 308 and separation from the cutting frame 102 (FIG. 2). The disposability of the blade frame 302 and cutting blade 306 eliminates the need for decontamination of the blade frame 302 between uses of the skin-harvesting device 100.

Figure 4:
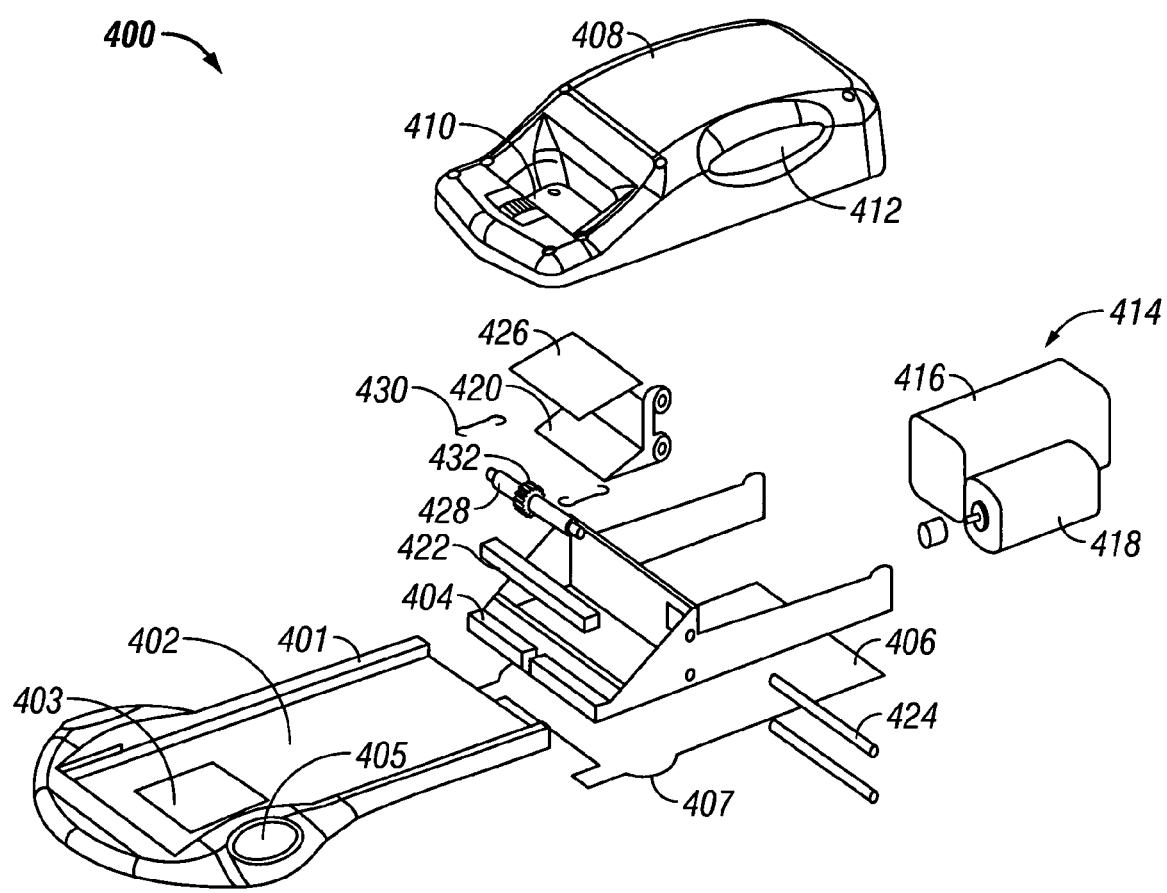
FIG. 4 is an exploded view of an alternate embodiment of the first aspect of the present invention.

Referring now to FIG. 4, an exploded view of an alternate embodiment of a skin-harvesting device 400 is shown. The skin-harvesting device 400 includes a base plate 402, and a frame base 404 connected to a frame 406 and adapted to slide in the base plate 402 via slide rails 401 positioned at lateral edges of the base plate 402. The base plate 402 further has a base window 403 at a forward end thereof, and base grips 405 positioned along lateral ends of the base plate 402. Slides 407 are provided at lateral edges of the frame 406 to engage the slide rails 401 and slide freely therethrough.

An ergonomic cover 408 is adapted to encompass the frame 406 and frame base 404, and has a cover window 410 at a forward end thereof that allows a user to see any skin harvested during use of the skin-harvesting device 400. Cover grips 412 are provided at lateral edges of the cover 408 and are adapted to allow a user to firmly grip the cover 408 and apply any pressure during use of the skin-harvesting device 400.

The frame 406 further supports a power source 414, such as a battery pack 416 and a motor 418 in a rear section, and a blade holder 420 and an adjustable depth plate 422 at a forward section. The blade holder 420 is coupled to the frame 406 via guide pins 424 or the like. The blade holder 420 further has a blade 426 coupled thereto. The blade 426 may be welded via thermoplastics or the like to the blade holder 420 to fix the blade at a predetermined angle with respect to the frame base 404. It is appreciated that other coupling means such as fasteners and the like may be used equivalently within the scope of this invention.

A cam 428 is positioned between the cover 408 and the adjustable depth plate 422, suitably secured thereto by a cam cover 430. The cam 428 further includes a cam dial 432 adapted to allow the user to raise or lower the adjustable depth plate 422 and thereby control the thickness of any skin harvested during use of the device.

Figure 5A:
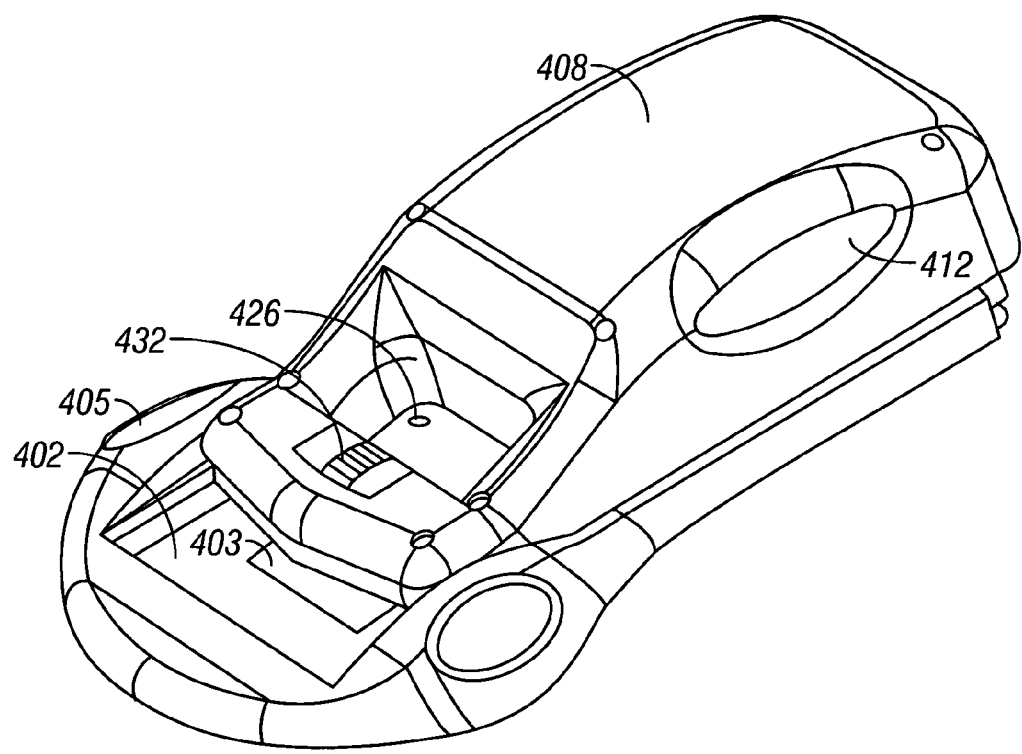
FIGS. 5A-5C are respectively the isometric top, side and bottom views of the skin-harvesting device of FIG. 4, respectively.
Figure 5B:
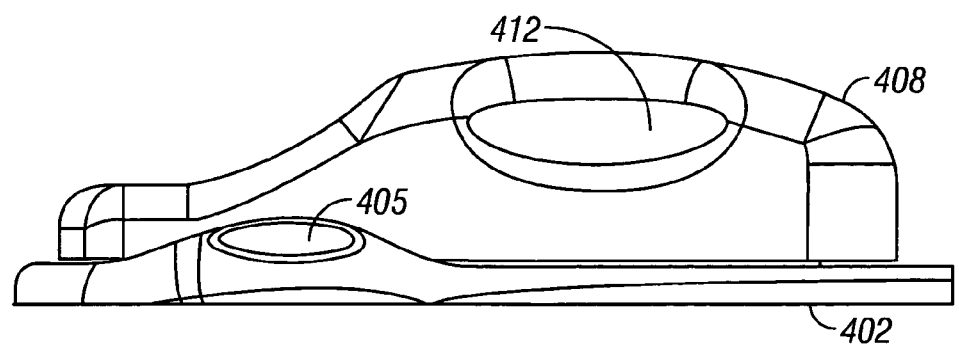
Figure 5C:
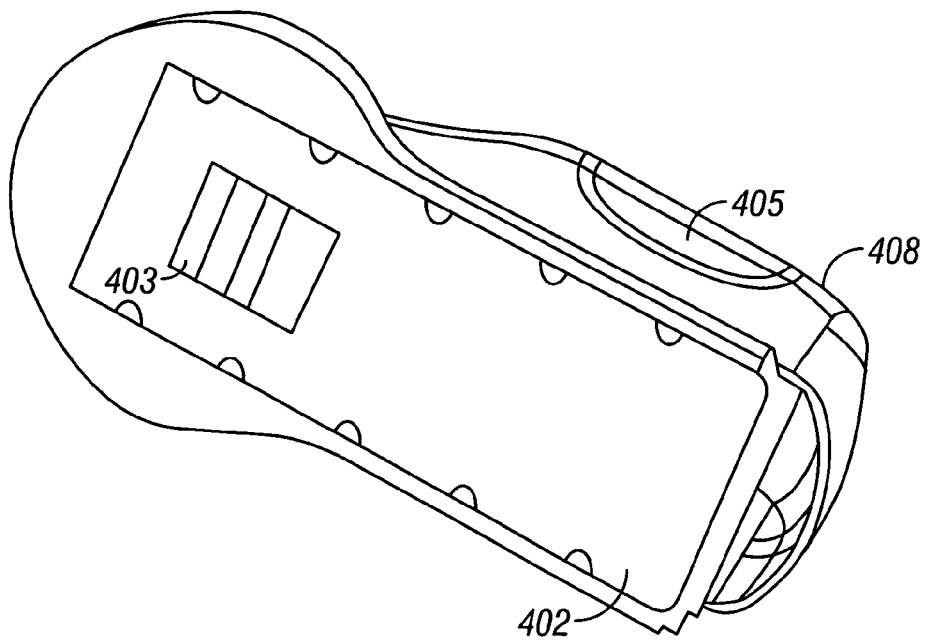

Referring now to FIGS. 5A-5C in combinations, isometric top, side and bottom views of the assembled skin-harvesting device 400 of FIG. 4 are shown. These views show the cover 408 and blade 426 as translated along the base plate 402 to a position either over or partially over the base window 403. The underside of the skin harvesting device as shown in FIG. 5C has the cover 408 advanced such that the blade 426 is aligned directly over the base window 403, as would be the case after skin has been severed from the harvest site. It is also to be appreciated that the cover 408 is adapted to provide the user with access to any harvested skin after removal of the skin.

Figure 6:
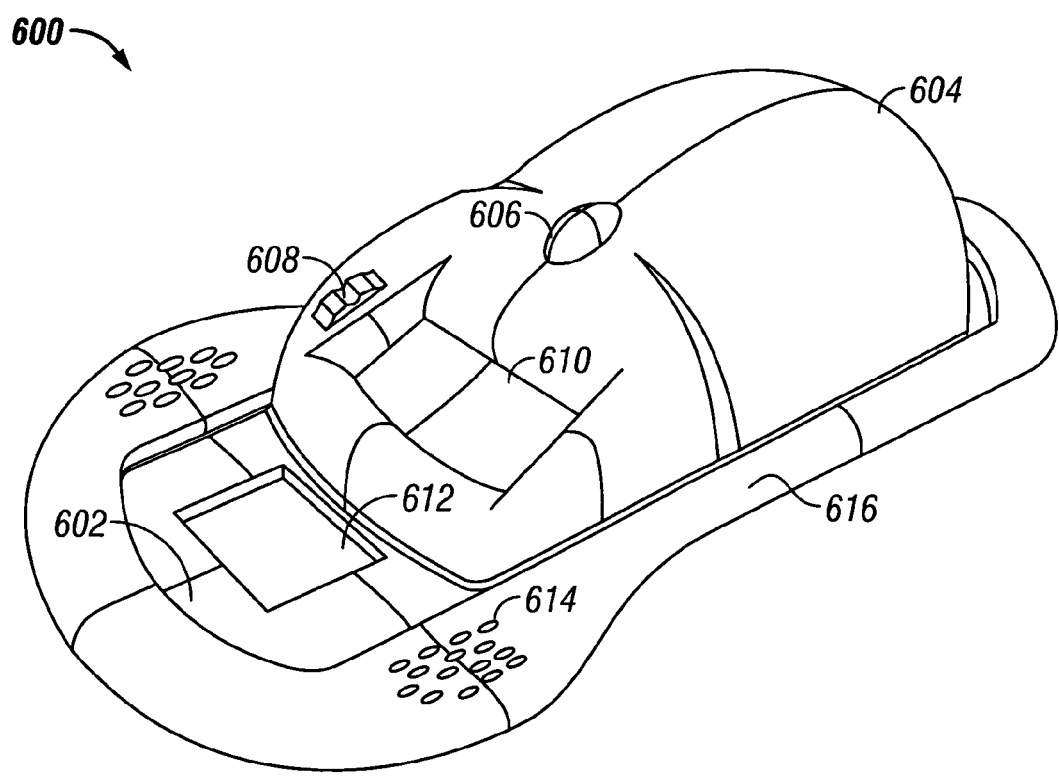
FIG. 6 is an isometric view of another alternate embodiment of the first aspect of the present invention.

Referring now to FIG. 6, an isometric view of another alternate embodiment of a skin-harvesting device 600 is shown. The skin-harvesting device 600 includes a base 602 and a cover 604, which contains the cutting blade and motor (not shown), and is adapted to translate within the base 602 in a manner similar to that described herein above. The cover 604 is adapted to ergonomically fit within the palm of a user's hand.

In this embodiment, an on/off switch 606 is positioned at an upper portion of the cover 604. Further, a skin-depth wheel 608 is positioned on the cover 604 adjacent a skin graft retrieval area 610 thereon, which is where skin collects after incision by the cutting blade. The skin-depth wheel 608 adjusts the adjustable depth plate (FIG. 3B, for example) and controls the thickness of skin collected for harvesting.

The base 602 includes the base window 612, which allows the user to see the skin prior to incision. In addition, the base 602 is provided with grip pads 614, which allow a user to grip the device 600 during operation. A full radius 616 is provided along the base 602 to assist the user during translation of the cover 604 and its associated components underneath.

Figure 7:
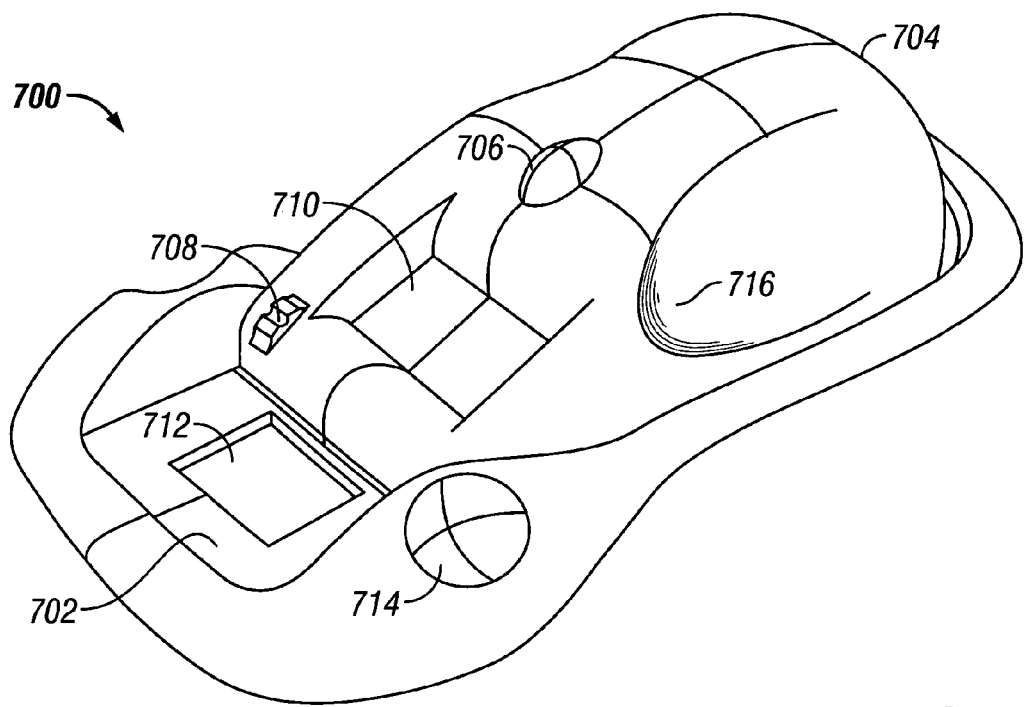
FIG. 7 is an isometric view of another alternate embodiment of the first aspect of the present invention.

Referring now to FIG. 7 an isometric view of yet another alternate embodiment of a skin-harvesting device 700 is shown. The skin-harvesting device 700 includes a base 702 and a cover 704, which contains the cutting blade and motor (not shown), and is adapted to translate within the base 702 in a manner similar to that described herein above.

An on/off switch 706 is positioned at an upper portion of the cover 704. A skin-depth wheel 708 is positioned on the cover 704 adjacent a skin graft retrieval area 710 thereon, which is where skin collects after incision by the cutting blade. The skin-depth wheel 708 adjusts the adjustable depth plate (FIG. 3B, for example) and controls the thickness of skin collected for harvesting.

The base 702 includes the base window 712, which allows the user to see the skin prior to incision. In addition, the base 702 is provided with large raised portions 714 on opposing sides, which allow a user to grip the device 700 during operation.

The cover 704 is adapted to ergonomically fit within the palm of a user's hand. The cover 704 further includes recesses 716 for a user's finger usable when a forward pressure is applied to the cover 704 to translate the cover 704 along the base 702.

Figure 8:
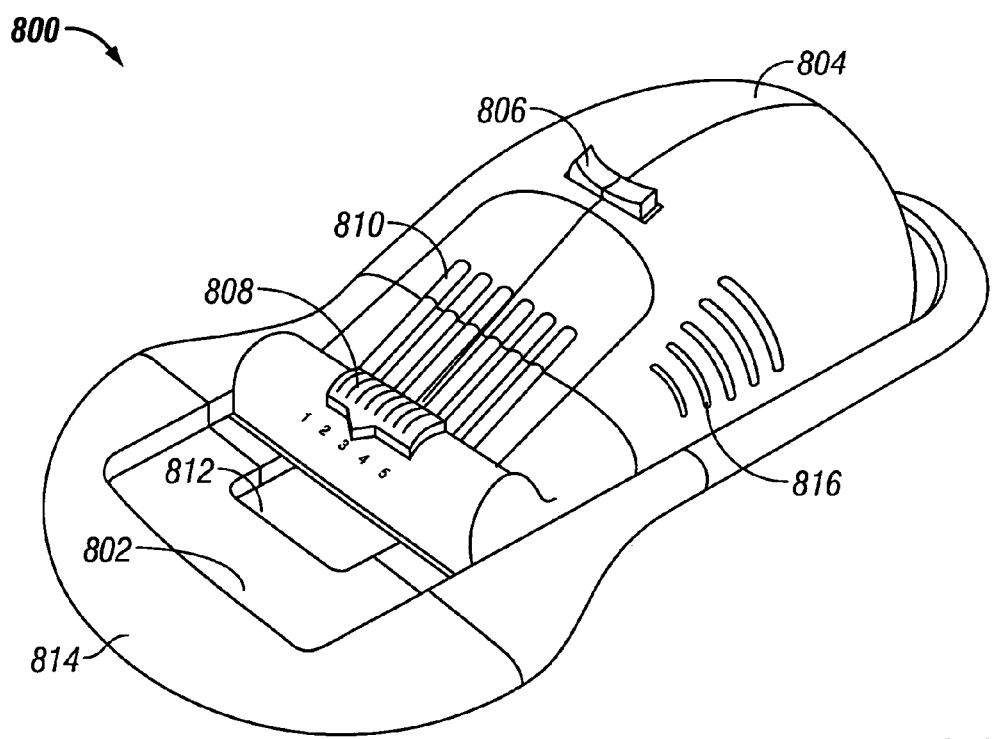
FIG. 8 is an isometric view of another alternate embodiment of the first aspect of the present invention.

FIG. 8 is an isometric view of another alternate embodiment of a skin-harvesting device 800. The skin-harvesting device 800 includes a base 802 and a cover 804, which contains the cutting blade and motor (not shown), and is adapted to translate within the base 802 in a manner similar to that described herein above.

An on/off switch 806 is positioned at an upper portion of the cover 804. A skin-depth slider 808 is positioned on the cover 804 adjacent a skin graft retrieval area 810 thereon, which is where skin collects after incision by the cutting blade. The skin graft retrieval area 810 is provided with one or more ridges to assist a user in removing any skin from the area 810 after harvesting.

The skin-depth slider 808 adjusts the adjustable depth plate (FIG. 3B, for example) and controls the thickness of skin collected for harvesting. Numbered indicia are provided to control the depth of incision on the cover 804 as adjusted by the skin-depth slider 808 and adjustable depth plate.

The base 802 includes the base window 812, which allows the user to see the skin prior to incision. In addition, the base 802 is provided with an extended area 814 on opposing sides, which provide a user with more area to grip the device 800 during operation.

The cover 804 is adapted to ergonomically fit within the palm of a user's hand. The cover 804 further includes textured portions 816 for a user's fingers usable when a forward pressure is applied to the cover 804 to translate the cover 804 along the base 802.

Figure 9:
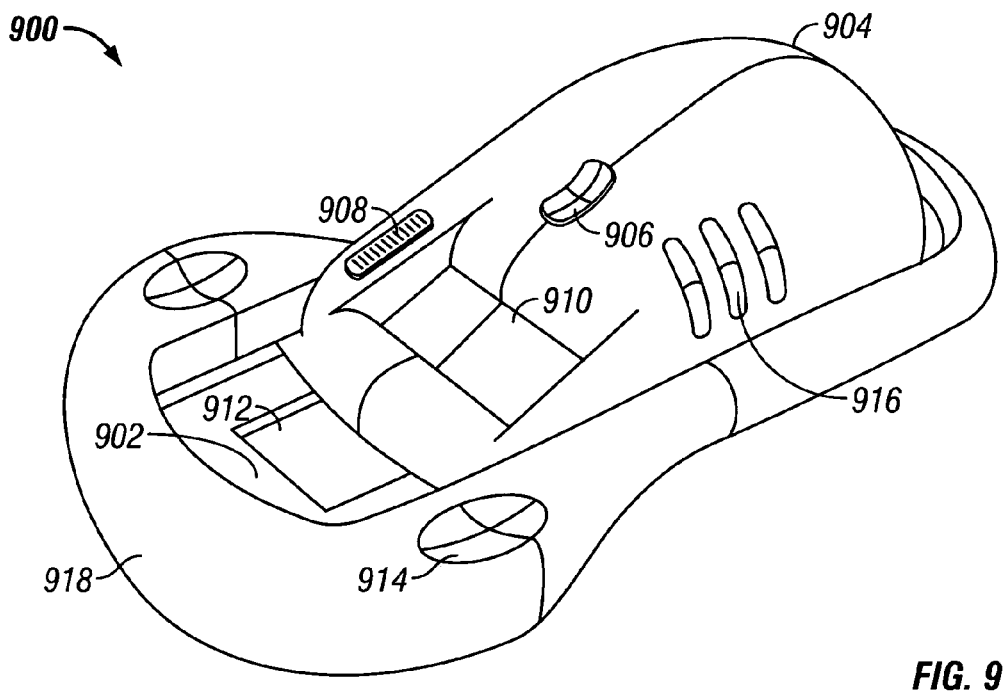
FIG. 9 is an isometric view of another alternate embodiment of the first aspect of the present invention.

Referring now to FIG. 9, an isometric view of still another alternate embodiment of a skin-harvesting device 900 is shown. The skin-harvesting device 900 includes a base 902 and a cover 904, which contains the cutting blade and motor (not shown), and is adapted to translate within the base 902 in a manner similar to that described herein above.

An on/off switch 906 is positioned at an upper portion of the cover 904. A skin-depth slider 908 is positioned on a lateral portion of the cover 904 adjacent a skin graft retrieval area 910 thereon, which is where skin collects after incision by the cutting blade. As in prior embodiments, the skin graft retrieval area 910 may be provided with one or more ridges to assist a user in removing any skin from the area 910 after harvesting.

The skin-depth slider 908 adjusts the adjustable depth plate (FIG. 3B, for example) and controls the thickness of skin collected for harvesting. Numbered indicia are provided on the lateral portion of cover 904 to indicate the depth of incision as adjusted by the skin-depth slider 908 and adjustable depth plate.

The base 902 includes the base window 912, which allows the user to see the skin prior to incision. The base 902 is adapted to be wider at portions adjacent the base window 912, and thicker throughout the circumference of the base 902 to be more accessible to the user. In addition, the base 902 is provided with a raised portion 914 on opposing sides on the thicker, wider area of the base 902 for providing a user with more area to grip the device 900 during operation.

The cover 904 is adapted to ergonomically fit within the palm of a user's hand. The cover 904 further includes textured portions 916 for a user's fingers usable when a forward pressure is applied to the cover 904 to translate the cover 904 along the base 902.

Figure 10:
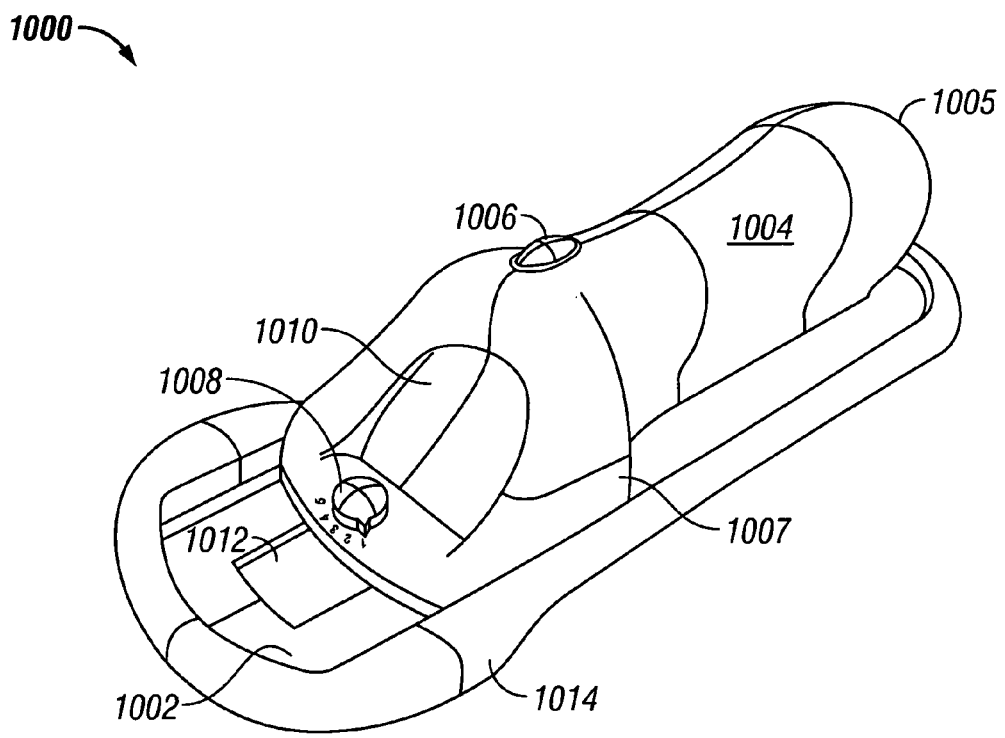
FIG. 10 is an isometric view of another alternate embodiment of the first aspect of the present invention.

Referring now to FIG. 10 an isometric view of another alternate embodiment of a skin-harvesting device 1000 is shown. The skin-harvesting device 1000 includes a base 1002 and a cover 1004, which contains the cutting blade and motor (not shown), and is adapted to translate within the base 1002 in a manner similar to that described herein above.

The skin-depth wheel 1008 adjusts the adjustable depth plate (FIG. 3B, for example) and controls the thickness of skin collected for harvesting. Numbered indicia are provided adjacent the skin-depth wheel 1008 to indicate the depth of incision as adjusted by the skin-depth wheel 1008 and adjustable depth plate.

The skin-depth wheel 1008 adjusts the adjustable depth plate (FIG. 3, for example) and controls the thickness of skin collected for harvesting. Numbered indicia are provided adjacent the skin-depth wheel 1008 to indicate the depth of incision as adjusted by the skin-depth wheel 1008 and adjustable depth plate.

The base 1002 includes the base window 1012, which allows the user to see the skin prior to incision. The base 1002 is adapted to be wider at portions adjacent the base window 1012, and thicker throughout the circumference of the base 1002 to be more accessible to the user. In addition, the base 1002 is provided with an enlarged portion 1014 on opposing sides of the base window 1012 for providing a user with more area to grip the device 1000 during operation.

The cover 1004 is adapted to ergonomically fit within the palm of a user's hand. In this embodiment, the cover 1004 is tubular, and has an enlarged forward section 1007, which is adapted to be manipulated by a user during translation of the cover 1004 along the base 1002 during incision activity. In addition, the enlarged forward section 1007 provides sufficient area for the skin graft retrieval area and is angled to allow collection of skin thereon.

Figure 11:
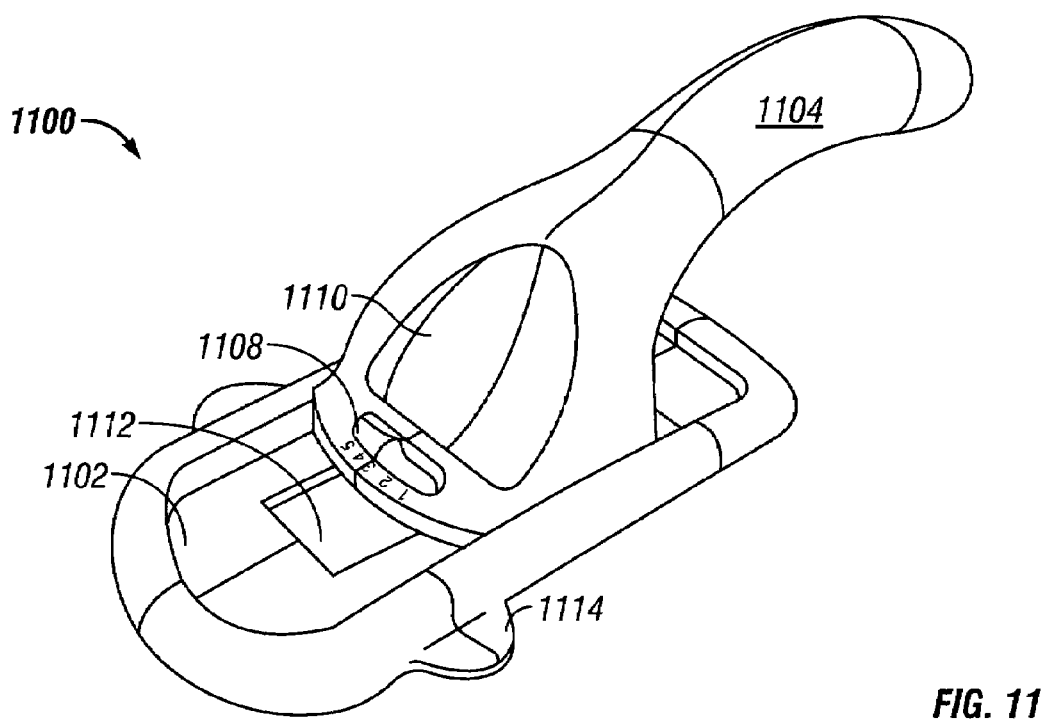
FIG. 11 is an isometric view of another alternate embodiment of the first aspect of the present invention.

Referring now to FIG. 11, an isometric view of another alternate embodiment of a skin-harvesting device 1100 is shown. The skin-harvesting device 1100 includes a base 1102 and a cover 1104, which contains the cutting blade and motor (not shown), and is adapted to translate within the base 1102 in a manner similar to that described herein above. Alternatively, the motor (not shown) may be external to the device 1100 and connected thereto to provide power.

The cover 1104 preferably comprises a handle-portion which has the on/off switch positioned at a lower surface thereof, and a skin-depth slider 1108 positioned adjacent a skin graft retrieval area 1110, which is where skin collects after incision by the cutting blade.

The skin-depth slider 1108 adjusts the adjustable depth plate (FIG. 3B, for example) and controls the thickness of skin collected for harvesting. Numbered indicia are provided adjacent the skin-depth slider 1108 to indicate the depth of incision as adjusted by the skin-depth slider 1108 and adjustable depth plate.

The base 1102 includes the base window 1112, which allows the user to see the skin prior to incision. The base 1102 includes tab portions 1114 adjacent the base window 1112 that allow the user's fingers area to apply even pressure to the base 1102 during use.

The cover 1104 is adapted to ergonomically fit within the palm of a user's hand and be gripped thereby. In this embodiment, the handle-portion of the cover 1104 is adapted to be firmly engaged by a user's hand during translation of the cover 1104 along the base 1102 during incision activity.

Figure 12:
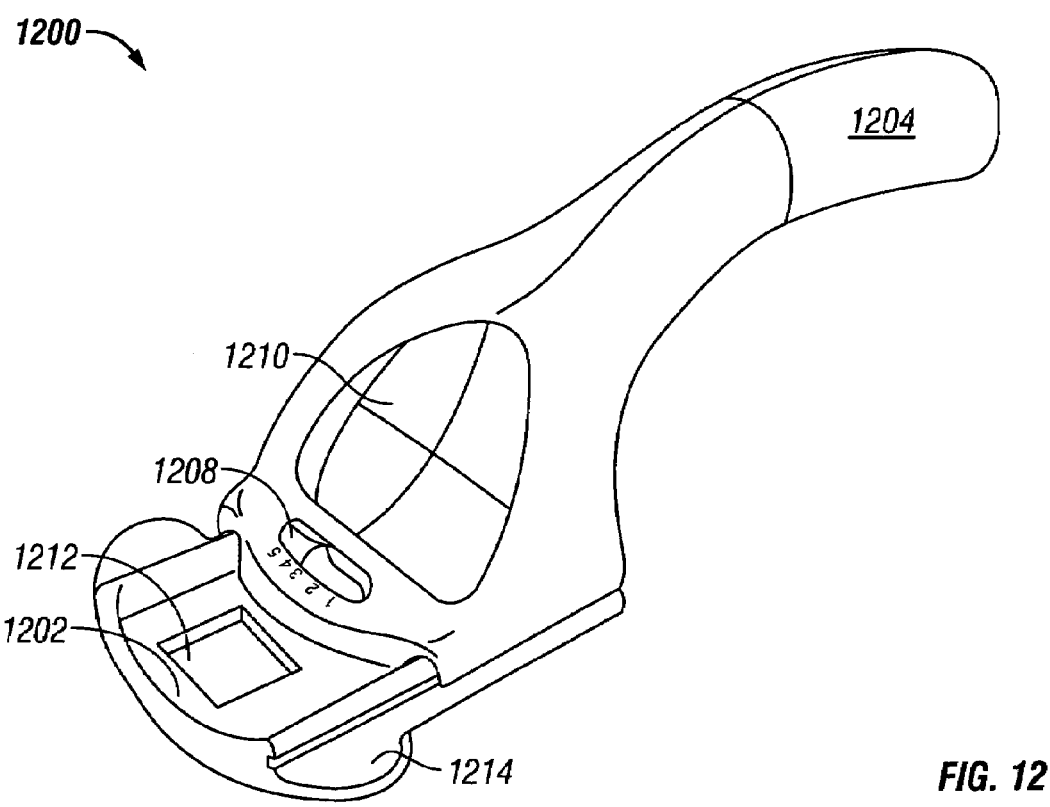
FIG. 12 is an isometric view of another alternate embodiment of the first aspect of the present invention.

Referring now to FIG. 12, an isometric view of another alternate embodiment of a skin-harvesting device 1200 is shown. The skin-harvesting device 1200 is substantially similar to the skin-harvesting device 1100 of FIG. 11, with like reference numbers denoting like elements.

The base 1202, however, is significantly shorter in length than the base 1102 of FIG. 11. The shortened base 1202 allows the user more flexibility in use of the device 1200, and assists the user when pressure is applied to the tabs 1214 of the base 1202 during incision operation. In addition, the base 1202 is open at one end, thereby allowing a user to move the cover 1204 within the base 1202 or to extract the cover 1204 (and related components, such as the motor and cutting blade) from the base 1202.

An on/off switch may be provided on a lower surface of the cover 1204. A skin depth slider 1208 is positioned adjacent a skin graft retrieval area 1210, which is where skin collects after incision by the cutting blade. The skin-depth slider 1208 adjusts the adjustable depth plate (FIG. 3B, for example) and controls the thickness of skin collected for harvesting. Numbered indicia are provided adjacent the skin-depth slider 1208 to indicate the depth of incision as adjusted by the skin-depth slider 1208 and adjustable depth plate.

Figure 13:
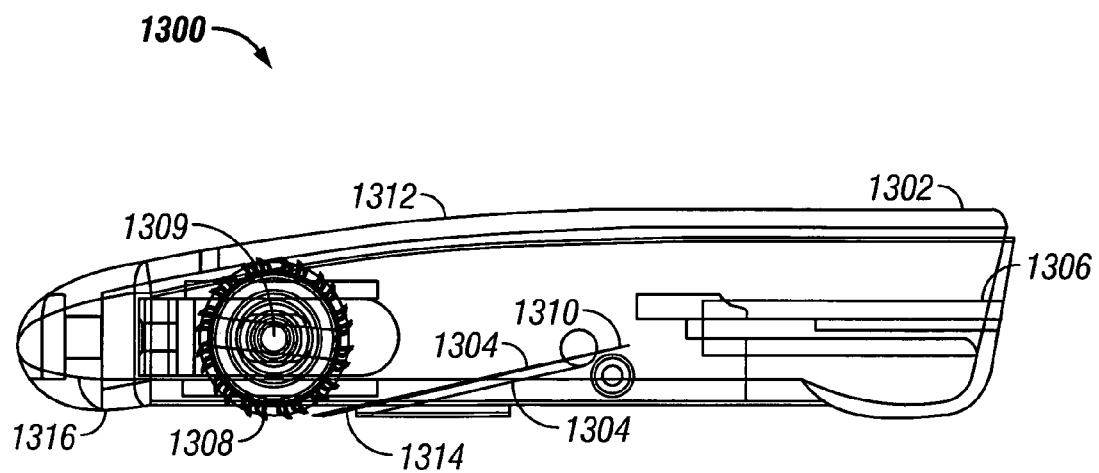
FIG. 13 is a side partial cross-section view of another embodiment of the first aspect of the present invention.

Referring now to FIG. 13, is partial cross-section view of a cover 1302 of another embodiment of a skin-harvesting device 1300 is shown. The cover 1302 houses a blade holder 1304, motor 1306 and a roller wheel 1308 coupled to the cover 1302 by an axle 1309. In addition, a cover window 1312 may be included at an area above the blade holder 1304, which has a blade 1314 positioned thereon. The roller wheel 1308 is positioned before the blade 1314 and blade holder 1304, and will be described in more detail herein below.

The cover 1302 further houses an adjustable depth plate 1316, which is positioned forward of the roller wheel 1308. The adjustable depth plate 1316 is adapted to control the thickness of any skin protruding through the base (not shown) during use of the device 1300.

Figure 14:
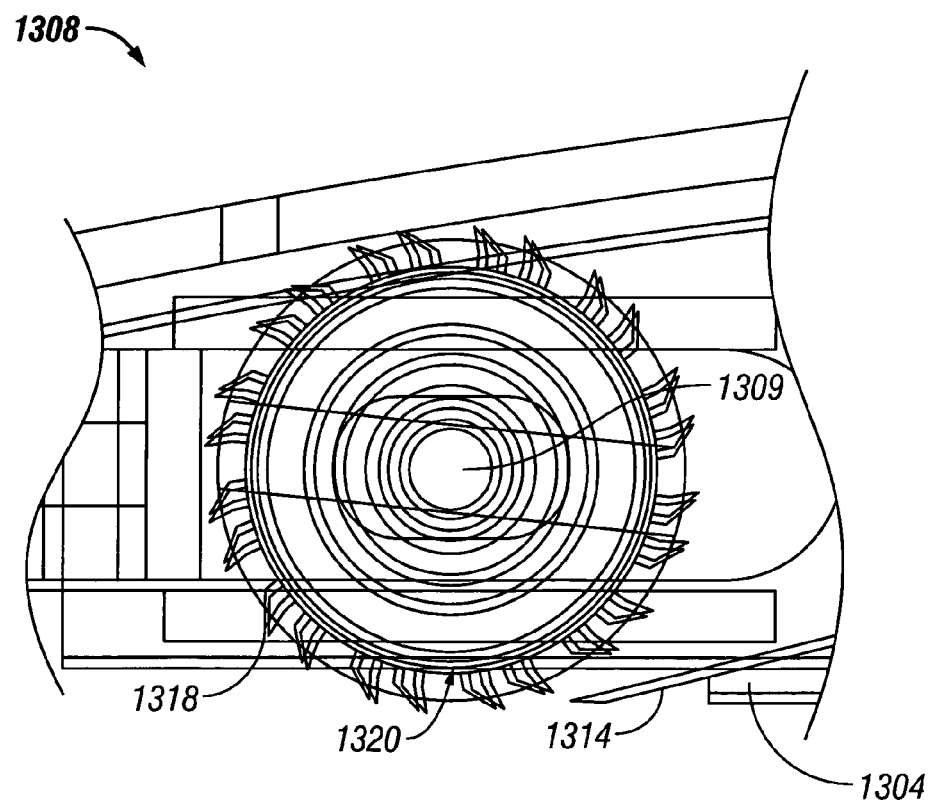
FIG. 14 is an enlarged side plan view of the roller of FIG. 13.

Referring now to FIG. 14, an enlarged side plan view of the cover 1302 and roller wheel 1308 of FIG. 13 is shown. The roller wheel 1308 includes small teeth 1318 that are used to puncture or hook the skin and hold it onto the roller wheel 1308 until it can be deposited on a mincer device. The teeth 1318 grip the skin and pull it over the blade 1314, which severs the skin. The severed skin is then rolled onto the roller wheel 1308 through the teeth 1318 engagement with the skin. The teeth 1318 extend from the outer circumference 1320 of the roller wheel 1308.

Because handling split thickness skin grafts can be a challenging and time-consuming process given that the skin tends to curl, which is further compounded by a user wearing sterile surgical gloves that reduce dexterity, the addition of a roller wheel 1308 that collects the harvest eliminates these burdens.

Figure 15:
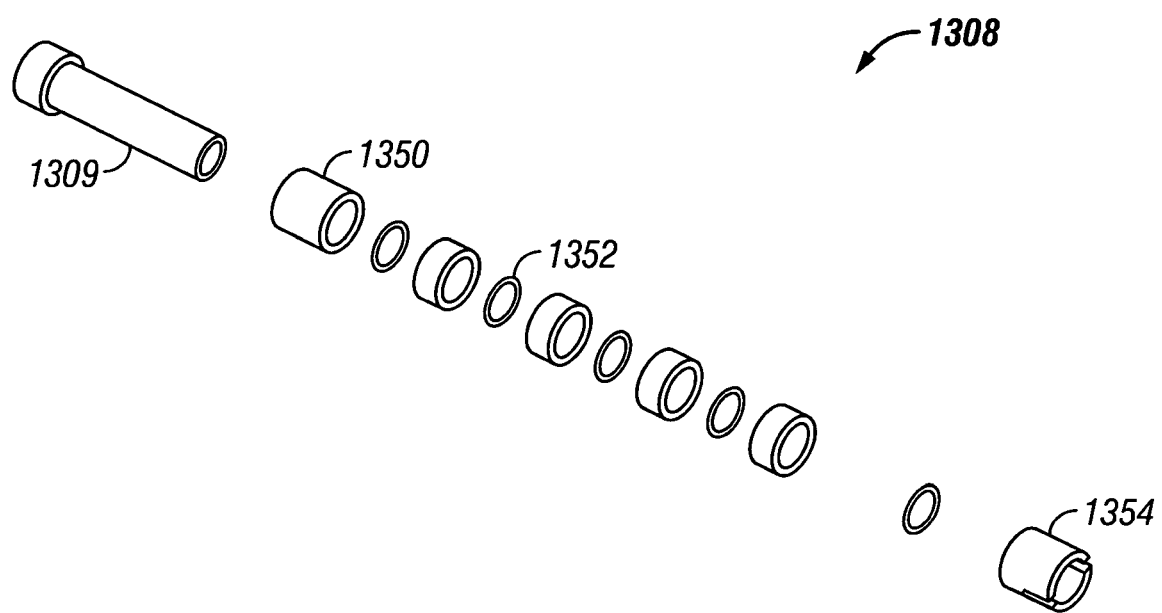
FIG. 15 is an exploded isometric view of the roller of FIG. 13.

Referring now to FIG. 15, an exploded isometric view of the roller wheel 1308 of FIG. 13 is shown. The roller wheel 1308 as coupled to the axle 1309 includes a plurality of spacer disks 1350 and roller segments 1352. The roller segments 1352 include teeth (FIG. 14) for gripping the tissue. The spacer disks 1350 provide a surface for collecting the tissue after the tissue is severed by the blade (FIG. 13). The axle 1309 may comprise a threaded bolt, and mate with a threaded segment 1354 provided in the roller wheel 1308.

The assemblies of the present invention in its many embodiments thereby provide a system for obtaining and processing tissue samples from a donor site having an area, e.g., of about 1 inch by about 1 inch in size, although other sizes may be suitably harvested, such that the vast majority of tissue processed at this size is viable when transplanted to a recipient site.

The simple design of the device substantially obviates the high-degree of user skill required by the current state of the art and thereby provides the potential to reduce overall costs and expense associated with the use for such dermatomes.

B. Tissue Processing

Figures 16A, 16B:
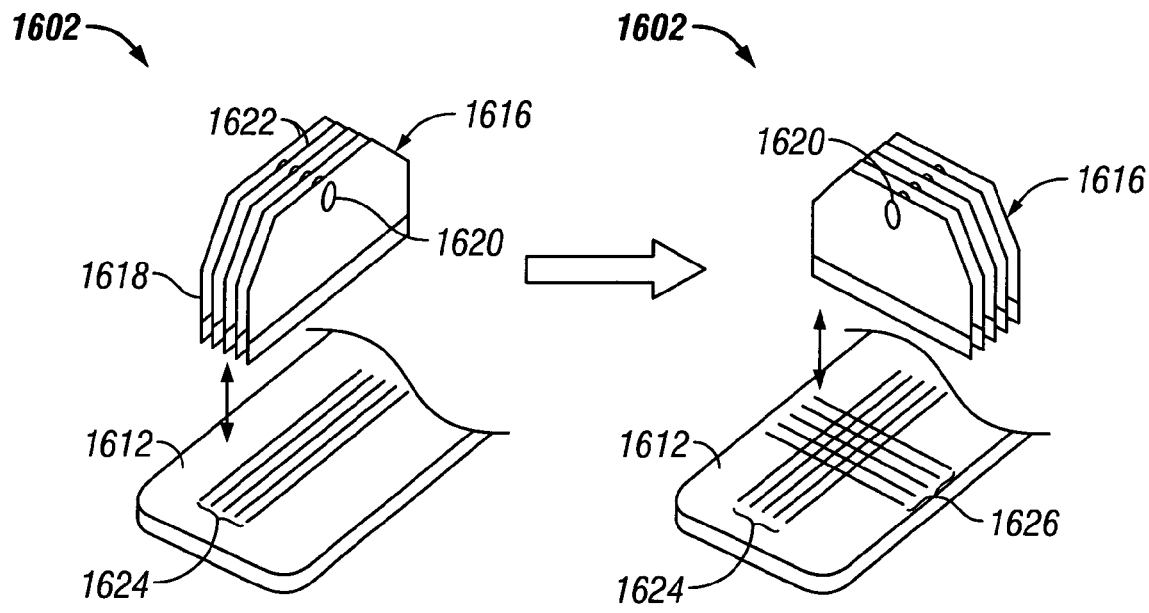
FIG. 16A and FIG. 16B are perspective views illustrating an embodiment of the tissue processor of the second aspect of the present invention.

After the donor tissue is removed from the donor site, the tissue may be processed by the tissue processor 1602, as illustrated in FIGS. 16A and 16B. The tissue processor is comprised of a series of sharpened blades 1618 arranged in parallel to one another and fixed along an axis 1620. The distance 1622 between the blades 1618 may be adjusted according to the desired size of the tissue sample to be obtained. In various embodiments of this aspect of the present invention, the distance 1622 between each blade 1618 is in the range of about 250 microns to 1000 microns. The blades may be set apart at a fixed distance, adapted to adjust to one of a plurality of fixed distances, or may be variably adjusted over a range of distances. Two sets of cuts are made into the donor tissue 1612. The first cut, as illustrated in FIG. 16A, create a first series of parallel cuts 1624 through the donor tissue 1612 when the processor is depressed into the tissue 1612. The second cut, as illustrated in FIG. 16B, create a second series of parallel cuts 1626 that are in perpendicular arrangement to first cuts 1624. In some embodiments, the first set of cuts 1624 are made by the user, who subsequently reorientates the processor 1616 to an angle about 90 degrees relative to the first set of cuts 1624 to make the second set of cuts 1626. In other embodiments, the processor 1616 may be automated to make the first set of cuts during a first pass of the processor across the donor tissue 1612, and then automatically reorientates the processor 1616 to an angle about 90 degrees relative to the first set of cuts 1624 to make the second set of cuts 1626. An electronic motor (not shown), as known in the art, may be utilized for automated rotation of the processor 1616. In such an embodiment, a switch (also not shown) may be integrated with the motor, wherein the switch is activated as the processor 1616 changes direction. Each change in direction of the processor 1616 causes the switch to activate the motor so as to rotate the processor 1616 within a housing. A subsequent change in direction of the processor, as in from left to right, will activate the switch, causing either the processor 1616 or the donor tissue 1612 to rotate 90 degrees from its existing position.

Figure 17:
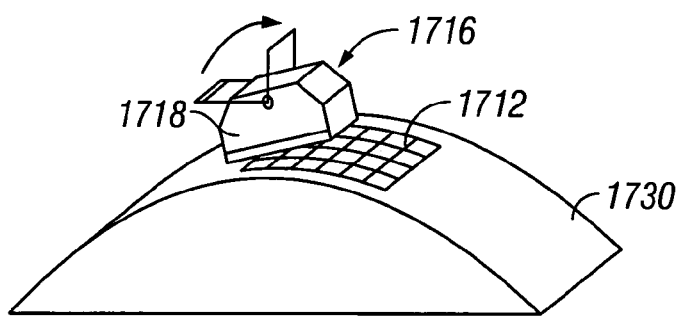
FIG. 17 is a perspective view of an alternative embodiment of the tissue processor of the second aspect of the present invention shown in use with a curved cutting surface.

As illustrated in FIG. 17 a cutting block 1730, having a convex configuration, may be utilized as a cutting surface. The convex cutting block serves to focus the pressure of the blades only at the point where the blades come in contact with the curved surface. This increases the ability to cut the STSG as it is easier to cut through a small portion of the graft versus the whole area of the graft at once. In use, the processor 1716 is rocked across the donor tissue 1712, which is supported by the block 1730, such that only a portion of the blades 1718 are in contact with the donor tissue 1712. The processor 1716 is rocked across the donor tissue 1712 such that an even distribution of cutting pressure is exerted across the surface of the donor tissue 1712.

Figure 18:
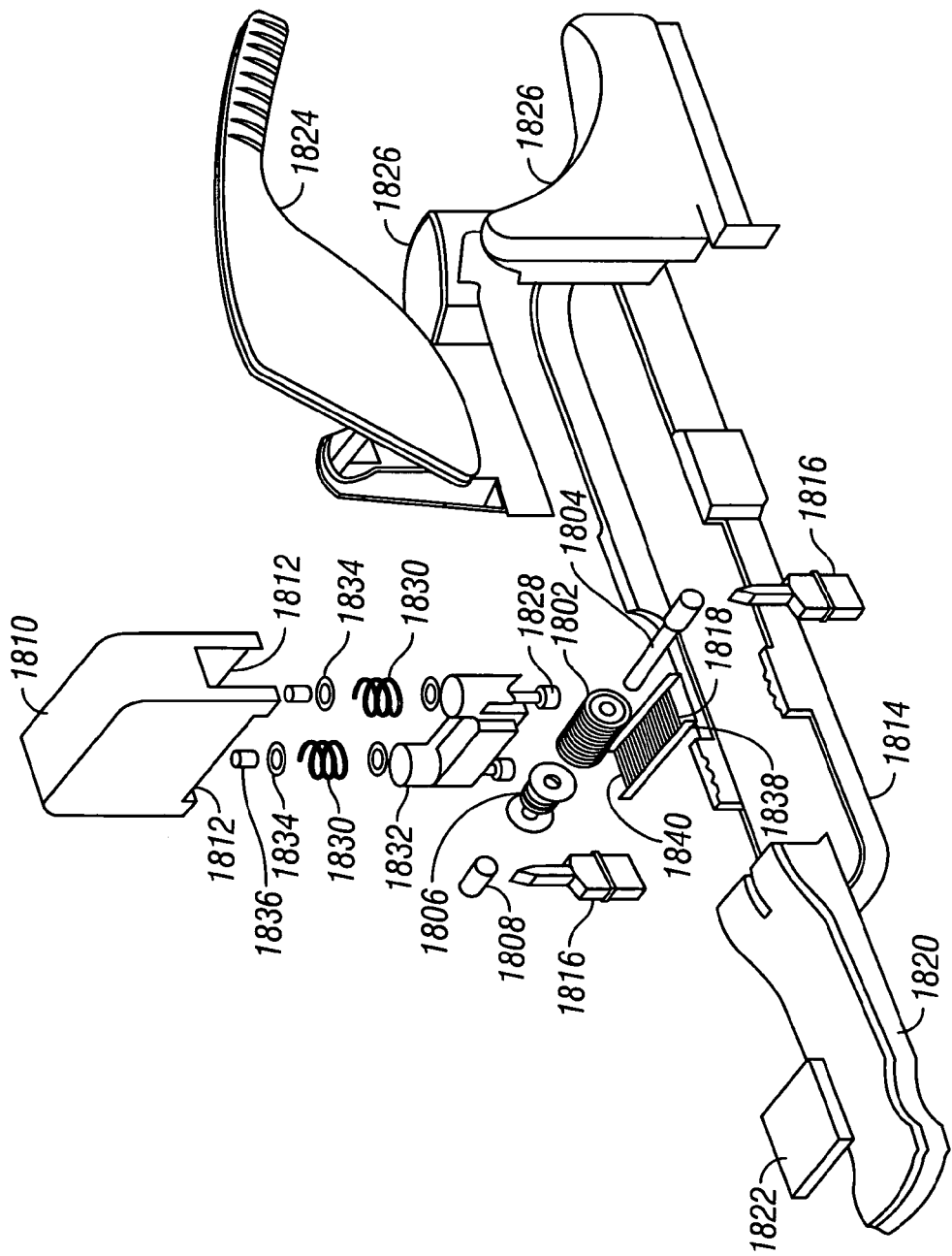
FIG. 18 is a perspective view of an embodiment of a tissue processor of the second aspect of the present invention which utilizes curved, or circular blades and cuts on a flat surface.

In another embodiment, as shown by FIG. 18, a set of blades, made up of a plurality of circular blades 1802, are aligned on a blade shaft 1804, with spacers 1806 positioned between the blades 1802 and a bushing 1808 at the end of the blade shaft 1804. The blades 1802 and shaft 1804 are covered by a housing 1810 which has a screen 1840 with a trailing edge 1838 that is fixed to the recessed bottom edges 1812 of the housing 1810. The housing 1810 is detachable connected to the base 1814 by the fasteners 1816. The screen 1840 has a number of slits 1818 disposed therein, that align with the blades 1802, which protrude in use (not shown) through the slits 1818. On the base 1814 is a sled 1820, upon which rests a removable cutting mat 1822. The sled 1820 and cutting mat 1822 are moved along the base by means of the handle 1824, that is held in position by the supports 1826. When a STSG (not shown) is placed on the cutting mat 1822, it is moved with the sled 1820 to the blades 1802 protruding (not shown) through the screen 1840. The mat 1822 is positioned relative to the blades 1802 such that the mat 1822 with the STSG (not shown) displaces the blades 1802 upwards, which via the bolts 1828 compresses the springs 1830 mounted in the blade press 1832 with the aid of the washers 1834 and inserts 1836. The compression springs 1830 allow the blades 1802 to be displaced until a predetermined force of the blades 1802 against the cutting mat 1822 is achieved. This force is sufficient to allow for cutting of the skin and is proportional to the diameter and number of the blades. In one embodiment with 44 blades with an 18 mm diameter, the predetermined force was about 80 lbs/inch2. After the STSG has passed through the blades once, the cutting mat is removed, turned 90° and passed again through the blades to thereby prepare skin nanografts of a substantially uniform square shape and size.

One factor in the increasing the ease and efficiency of producing nanografts, is for the STSG and skin pieces to remain adhered to the mat and not to the cutting blades. In this regard, the cutting mat, the mat is made of a substance, or coated such, that the surface has hydrophilic properties. One suitable material type are polyether block amide resins, such as PEBAX® 7033, produced by Autofina, Philadelphia, Pa. The tactile properties of the mat can also be manipulated by surface texture. One suitable texture uses a 38 μm deep pore.

Figure 19A:
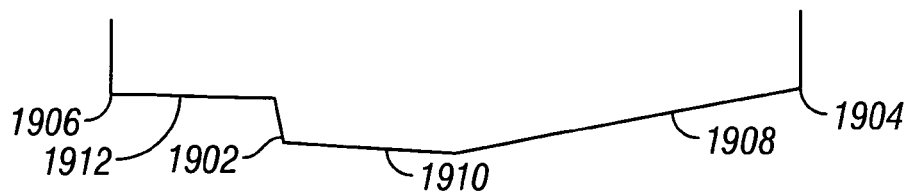
FIG. 19A-19C show respectively the side plan, isometric and plan view of an embodiment of a screen of the second aspect of the present invention.
Figure 19B:
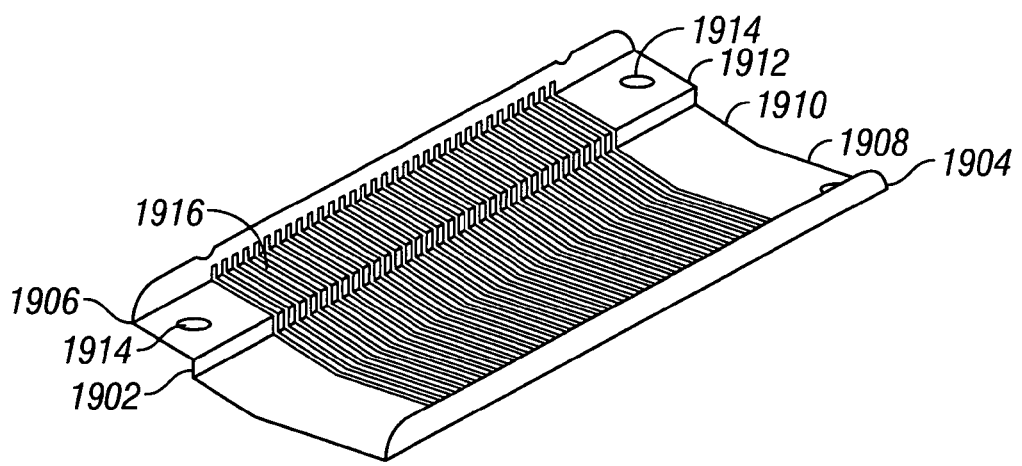
Figure 19C:
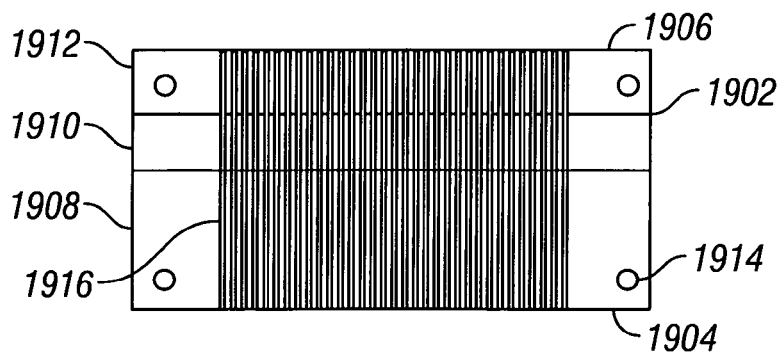

One embodiment of a technique to aid in the removal of skin pieces from the blades relates to the shape of the screen. In regard to FIG. 19, wherein FIG. 19A shows a side-plan view, and FIG. 19B an isometric view, and FIG. 19C a plan view of a screen, the step 1902 facilitates the extrusion of skin after it is cut by the blades (not shown) that protrude during use through the screen's slits 1916. The excised skin sample approaches the screen at the leading edge 1904, and, describing the shape of the screen from the leading edge 1904 to the trailing edge 1906, the screen describes a descending plane 1908 relative to the horizontal plane of the side-plan. This angle of the descending plan may be in the range of 5 to 15°, wherein it may be 8°, 9°, 10°, 11°, 12°, 13° or 14°. The screen shape then progresses to a generally horizontal section 1910, wherein generally horizontal means in regard to this embodiment of the invention, ±5° from the horizontal plane of the side plan view. The screen shape progresses thereon to a generally right angle step portion 1902. The vertical section of the generally right angle step portion may vary from 90° relative to the horizontal section, for example by 4 or 5°. The shape of the screen then describes a generally horizontal plane 1912 to the trailing edge 1906. The holes 1914 shown in the plan view facilitate the coupling of the screen to the housing.

Figure 20A:
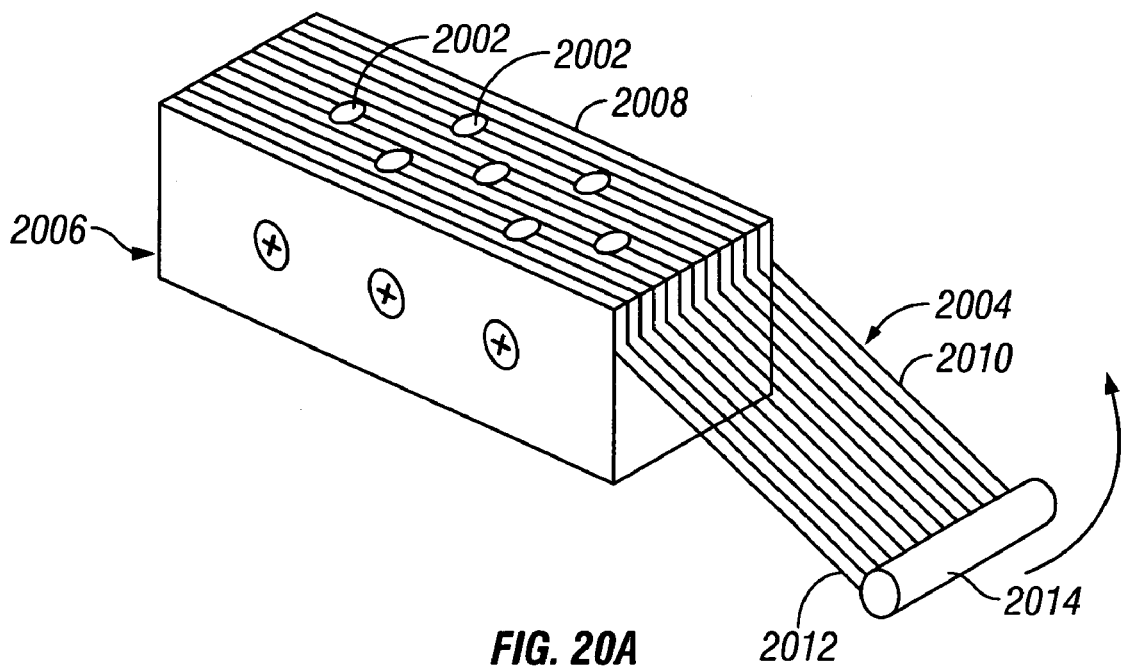
FIG. 20A and FIG. 20B are perspective representations of an embodiment of a tissue extractor of the second aspect of the present invention.
Figure 20B:
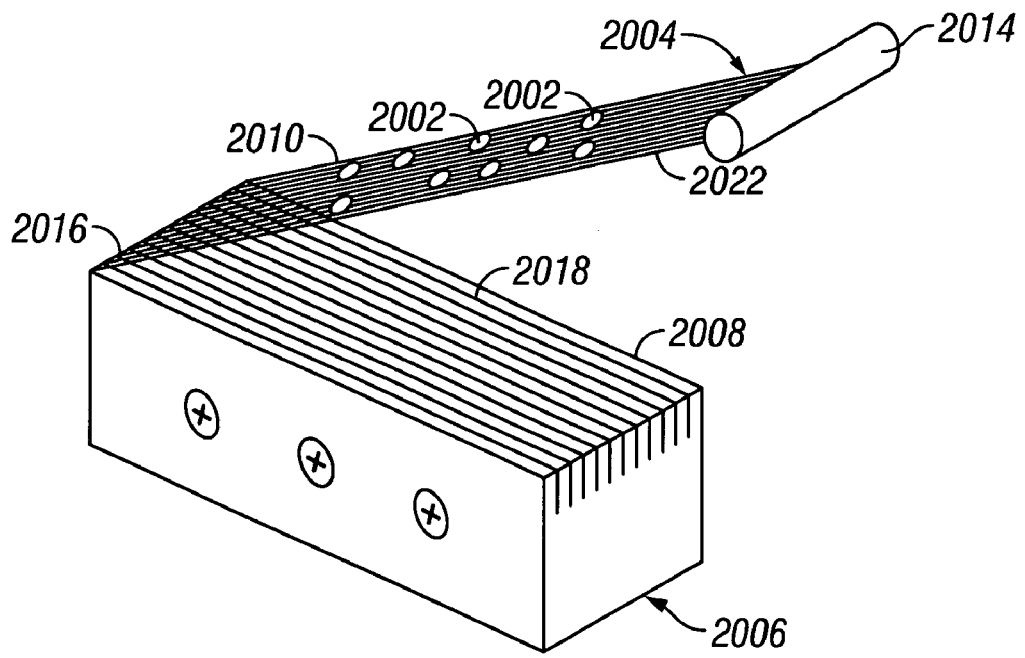

Turning now to FIGS. 20A and 20B, there is illustrated a tissue extractor 2004 for removing the processed tissue 2002 after it has been processed by the tissue processor 2006 into the appropriate size. The tissue extractor 2004 allows for the processed tissue 2002 to be easily removed from the blades 2008 of the processor 2006. In a typical application, the small size of the processed tissue 2002 may cause it to be trapped between the blades 2008 of the processor, and cause difficulty in retrieving for subsequent placement at the donor site. The tissue extractor 2004 consists of a series of strands 2010 arranged in parallel, and secured at a distal end 2012 to a handle 2014. The proximal end 2016 of the strands 2010 may be secured to the processor, such that as the extractor 2004 is pulled through the blades 2008, the proximal end 2016 of the strands 2010 remain secured to the processor 2006. The strands 2010 are arranged such that each individual strand 2010 occupies the spaced between each blade 2008, and are positioned below the cutting surface of the blades 2018 during application of the processor to the donor tissue 2002. After processing of the donor tissue 2002, the extractor 2004 is pulled upward from its handle 2014. In this process, the processed tissue 2002 is captured by the strands 2010 of the extractor 2004, creating a screen for pulling the processed tissue 2002 away from the blades 2008. The processed tissue 2002 may then be wiped, washed or otherwise removed from the extractor 2004 for placement on the recipient site.

C. Application of Skin Particles to the Wound Site

The third aspect of the present invention provides methods and devices to aid in the transfer of micrografts, including nanografts, to the wound site wherein relative to mechanical spreading the extent aggregation is decreased and the relative degree of even distribution is increased. These methods also aid in reducing the time required to perform the procedure, which when combined with other aspects of the present invention, assist in removing the grafting process from the operating room. Various embodiments of this aspect of the invention also provide for the advantages of negative pressure wound therapy to be integrated with skin grafting.

Embodiments of this aspect of the present invention encompass methods and devices wherein micrograft particles are suspended in a physiologically compatible aqueous solution then deposited on a transfer substrate, wherein the transfer substrate has the properties of a particulate filter, i.e., the micrograft particles are of a size that they will not pass through nor substantially into the transfer substrate. In some embodiments the transfer substrate is a non-adherent mesh or filter, i.e., will not adhere to the wound surface. Suitable examples are nylon and polypropylene meshes with pores of about 100 μm. In some embodiments the transfer substrate is a fibrous growth enhancing matrix as described in Section D infra.

In some embodiments the aqueous solution comprises an isotonic solution or physiological compatible buffer as are know in the art, e.g., phosphate buffered saline. Because the particles settle rapidly in these types of aqueous solutions, and to facilitate even disbursement of these particles, the particles may be agitated upon addition to the physiologically compatible solution to form a relatively even suspension. This procedure is preferably performed using sterile/aseptic techniques as are known in the art. The solution may optionally include and antibiotic.

Figure 21:
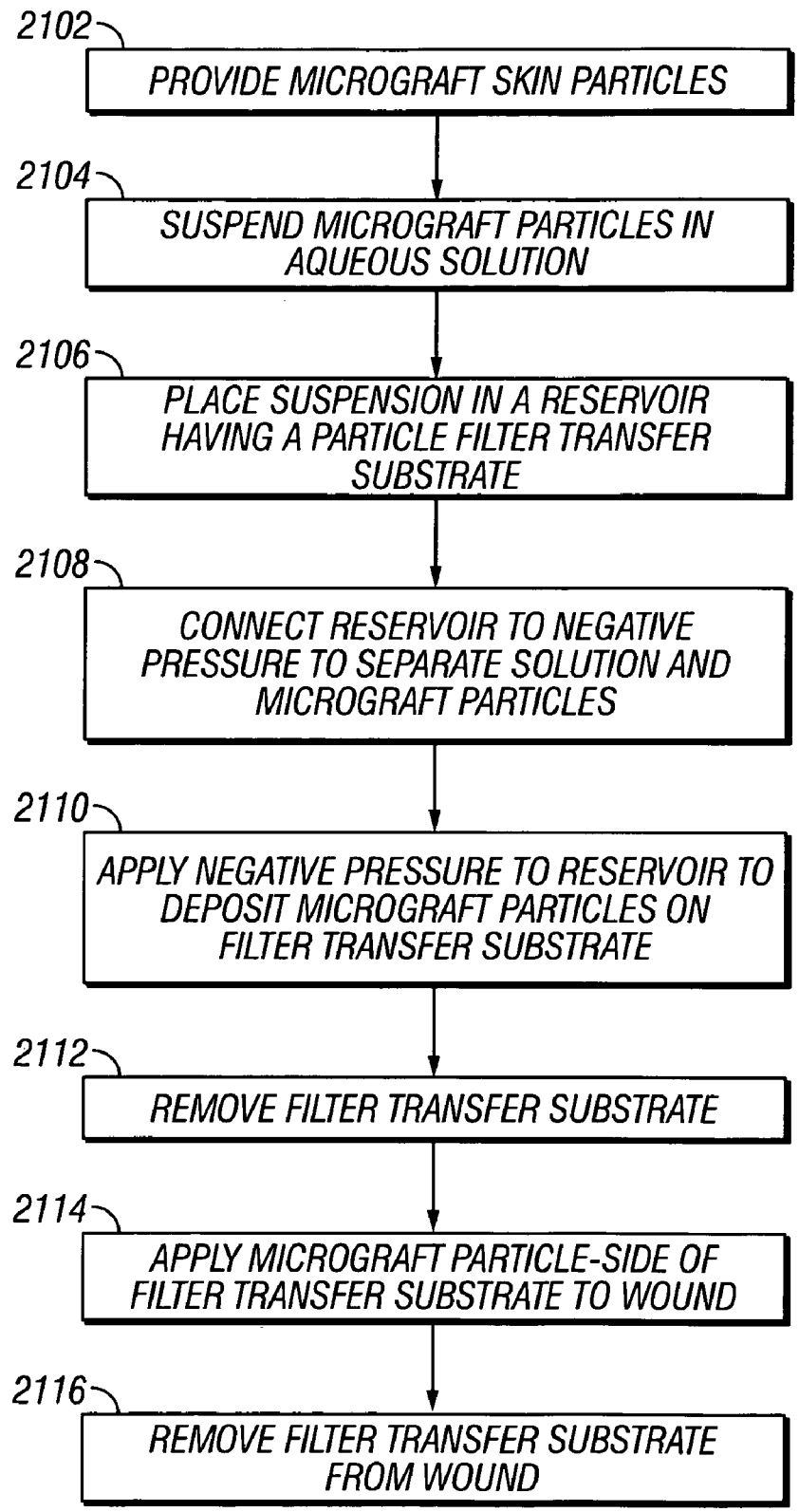
FIG. 21 is a schematic representation of one embodiment of the third aspect of the present invention, wherein negative pressure is used to deposit skin particles on a transfer substrate.

One such embodiment that overcomes the clumping or aggregation of skin micrograft particles is exemplified in schematic form in FIG. 21. First, minced-skin particles are provided, indicated by 2102, e.g., as previously described by the second aspect of the present invention. Wherein nanografts of a substantially uniform size and square shape are used, they are suitably sized and in a range of about 600 μm, though they may range in size from about 250 μm to about 1000 μm. Next, the minced skin particles are suspended in a physiologically compatible aqueous solution, indicated by 2104. The suspension of particles may take place via agitation or any other suitable means to adequately suspend the minced skin within the aqueous solution. The suspension is then placed in a reservoir having a particulate filter transfer substrate, indicated by 2106.

The reservoir is next connected to a negative pressure source, indicated by box 2108. The negative pressure source may be any suitable negative pressure source capable of separating the suspended minced skin particles from the solution. Preferably, the negative pressure source is located below the filter, the filter separating the solution from the negative pressure source. Negative pressure is next applied to the reservoir, thereby separating the solution from the suspended particles and depositing the suspended particles onto the filter, as indicated by box 2110. After separation, the filter is removed, indicated by box 2112. This process is exemplified in Example 2 and FIG. 29, infra. Next, the particle-containing side of the filter is applied to a wound, indicated by box 2114. The particles are transferred to the wound upon application. Finally, the filter is removed from the wound, which now has sufficiently even-spaced skin particles thereon, indicated by box 2116.

When suspended in aqueous solution, the particles are less likely to interact with each other, probably in part because the surface tension is reduced between particles. This method eliminates the gas to liquid interface, which likely contributes to particle clumping. With mechanical spreaders, there is a tendency for the particles to be mixed with wound fluids as they are applied, leading to protein binding between the particles. With this filter transfer substrate-based technology, the particles are separated, and when applied to the wound bed, are bound to the wound surface through a similar protein-based adhesion instead of to other particles.

In some embodiments, a super-absorbent sponge or polymer transfer substrate is used as the transfer substrate. The sponge or polymer removes the physiologically compatible suspension medium by absorption, leaving the micrograft particles deposited on the surface of the sponge or polymer. This can then be applied to a wound site.

Figure 22:
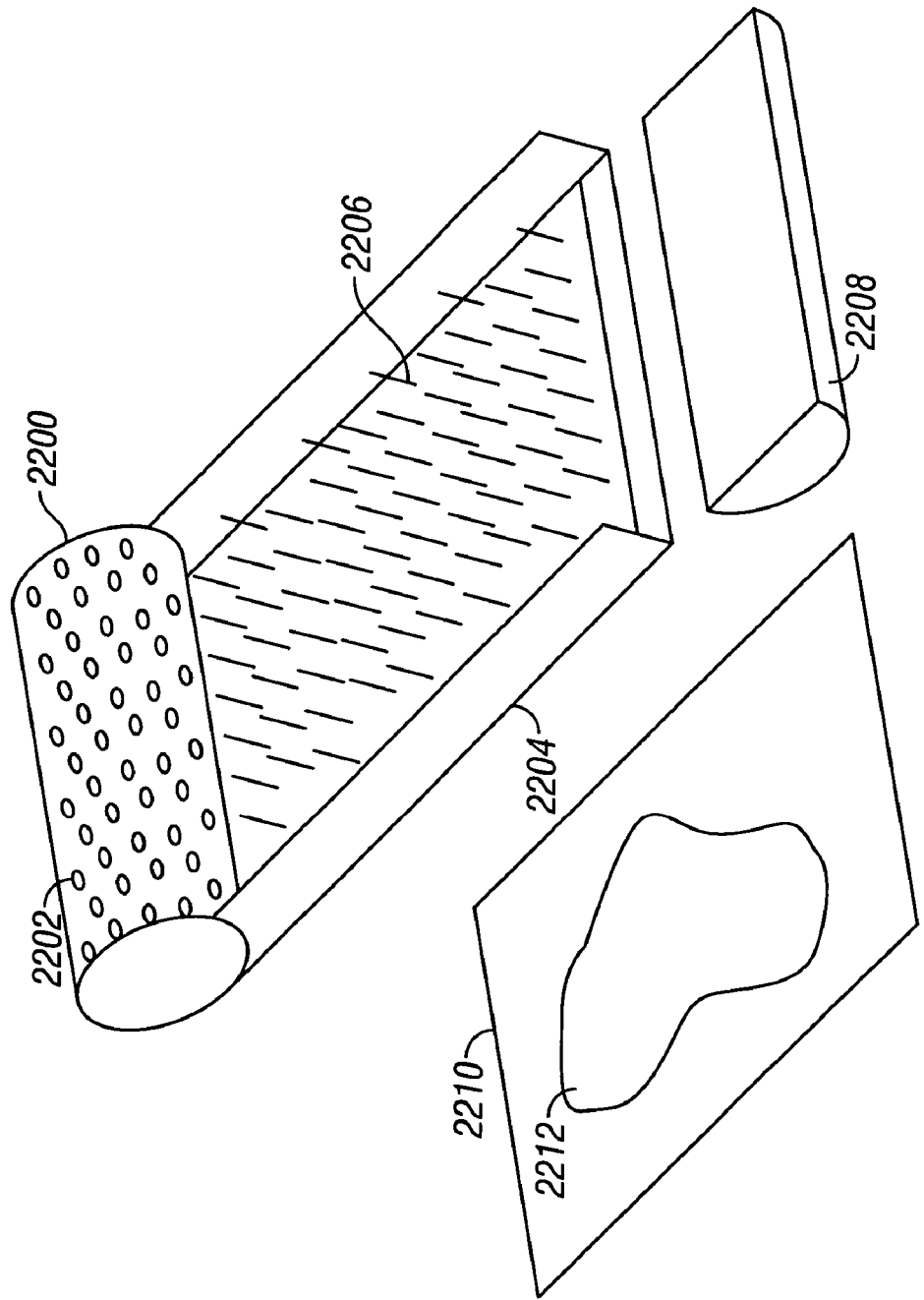
FIG. 22 is an isometric view of an alternative embodiment of the third aspect of the present invention, wherein a drain box is utilized to disperse skin particles prior to transfer to a transfer substrate.

Referring now to FIG. 22, an isometric view of yet another embodiment employing a transfer substrate. In this embodiment, an aqueous solution 2200 having micrograft skin particles 2202 suspended therein is poured through a drain box 2204. The drain box 2204 has a plurality of hooks 2206, similar to those in hook and loop fasteners, adapted to capture one or two particles 2202 per hook as the solution 2200 passes thereby. Alternatively, depressions or divots (not shown) may be formed in the drain box 2204 to capture the particles 2202 as the solution 2200 passes over. Particles 2202 not captured empty from the drain box 2204 into a collection gate 2208, where they may be re-used for subsequent capture.

In some embodiments, prior to particle capture, a mask 2210 that describes a cut-out area that corresponds to the area of a wound site, is positioned on the hooks or divots. The mask thereby covers that portion of the hooks or divots that do not correspond to the wound area. In this way micrograft particles are collected by hooks or divots that are confined to an area geometrically similar to that of the wound.

Figure 23:
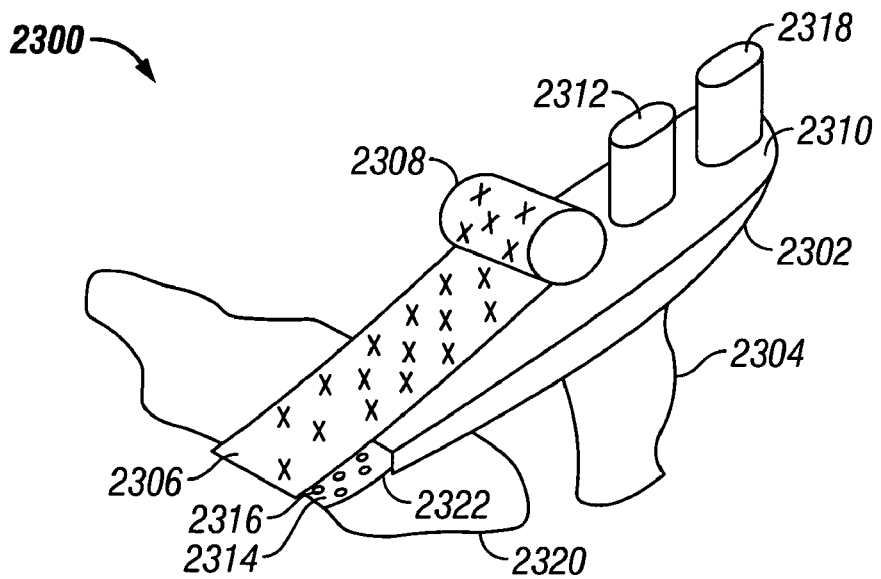
FIG. 23 is an isometric view of another embodiment of the third aspect of the present invention wherein skin particles are dispensed onto a mesh roll.

In an alternative embodiment, gel in addition to a physiologically compatible aqueous solution may be used to suspend the nanografts. Referring now to FIG. 23, an isometric view of a nanograft applicator 2300 is shown. The applicator 2300 includes a dispenser portion 2302 and a handle 2304 connected to the bottom of the dispenser portion 2302. A mesh 2306 is dispensed from the top surface of the dispenser portion 2302, which retains the mesh roll 2308 by a roller bracket 2310 or the like. A gel canister 2312 is connected to the dispenser portion 2302 for supplying gel 2314 into the dispenser portion 2302. The gel 2314 may have minced skin particles 2316 suspended therein, or minced skin particles 2316 may be provided in a minced skin canister 2318, which may contain an aqueous solution therein for suspending the minced skin particles 2316. The gel canister 2312 is removable and replaceable once all gel 2314 has been utilized. Likewise, if a minced skin canister 2318 is utilized, the minced skin canister 2318 may be removed and replaced once all solution has been utilized.

The rate of application, or how fast the applicator 2300 is moved over a wound 2320 has the potential to influence the thickness of the gel layer and hence the numbers of particles 2316 that are laid down on the wound 2320. Thus, the rate of application is preferably related to the rate of gel extrusion. To cover a wound 2320, the mesh 2306 is adhered to the periphery of the wound 2320 and pulled across the wound 2320. As the mesh 2306 is pulled across the end of the dispenser portion 2302, the gel 2314 having minced skin particles 2316 is extruded out of the dispenser portion 2302 onto the mesh 2306 through a dispenser opening 2322. Once the wound 2320 has been covered, the gel 2314 seeps through the mesh 2306 to the outer surface and may be removed by dressings. The minced skin particles 2316 remain on the wound 2320 and act as skin graft locations. The mesh 2306 may be torn after application to the wound 2320, and the process repeated until the wound 2320 is covered by skin particles 2316 evenly dispersed and applied on the wound 2320 and held to the wound 2320 via the mesh 2306. A similar mechanism will be described in more detail below.

Figure 24A:
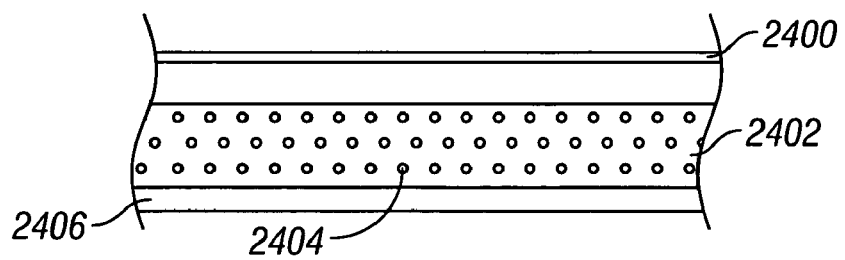
FIGS. 24A and 24B are cross sections of another embodiment of the third aspect of the present invention.

Referring now to FIG. 24A, a side cross-section view of a wound-site utilizing an alternate embodiment of the present invention is shown in a first stage. A mesh 2400 is positioned above a gel particle suspension 2402 having minced skin particles 2404 suspended therein. The gel particle suspension 2402 preferably is applied to a wound bed 2406 via a suitable applicator, such as the one showed in FIG. 23. Preferably, the skin particles 2404 are mixed into the gel either by light polymerization, which locks the particles 2404 in position and increases the gel's viscosity, or by auto-mixers. Epoxy mixing systems may be used without departure from the scope of the present invention.

Figure 24B:
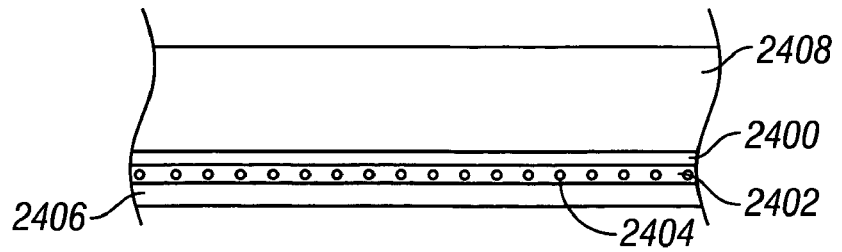

Referring now to FIG. 24B, which is another cross-section view of the wound-site of FIG. 24A is shown in a second stage. Regardless of the suspension characteristics, the gel particle suspension 2402 is covered by the mesh 2400, which functions to separate the minced skin particles 2404 from the gel 2408, thereby depositing the skin particles 2404 onto the wound bed. The gel is then removable via evaporation, moist dressing removal or the like, depending on the characteristics of the gel.

Figure 25A:
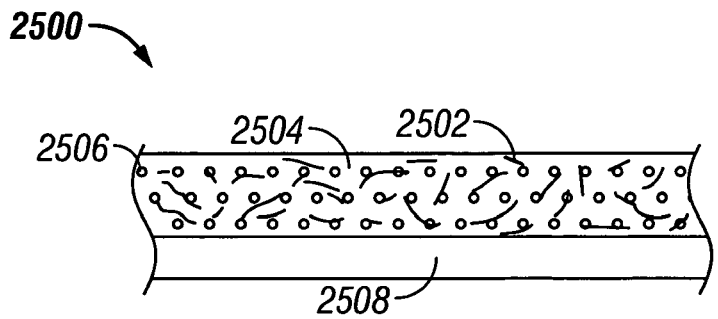
FIGS. 25A and 25B are cross sections of another embodiment of the third aspect of the present invention.

Referring now to FIG. 25A, a side cross-section view of a wound-site utilizing an alternate embodiment of the present invention is shown in a first stage. In this embodiment, a two-phase matrix 2500 of fiber 2502 and gel 2504 is used, having minced skin particles 2506 interspersed therein. The two-phase matrix 2500 is deposited onto the wound-site 2508 via an applicator, such as the one shown in FIG. 23. The gel 2504 is adapted to evaporate or dissolute after being exposed to the environment a predetermined period of time.

Figure 25B:
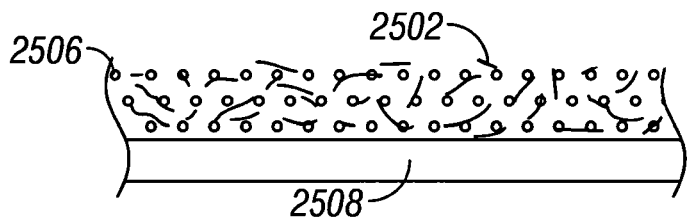

Referring now to FIG. 25B, a side cross-section view of the wound-site of FIG. 25A is shown in a second stage. At this point, the gel 2504 has undergone evaporation or dissolution, thereby leaving the fiber 2502 in a matrix form with the skin particles 2506 evenly interspersed therein. The skin particles 2506 are thus provided with the scaffold of the fiber matrix for outgrowth and formation of new epithelium, without the need for a mesh or other additional materials.

D. Negative Pressure Therapy

One aspect of the present invention is a biocompatible wound dressing for use with negative pressure therapy. As used herein, the term "pad" refers to foams, such as open-cell reticulated porous foams, screens and other porous-like materials. The term "conventional pad" refers to polyurethane (PU) or polyvinylalcohol (PVA) foams commonly used with V.A.C.® therapy. The term "V.A.C.® therapy" as used herein, refers to negative pressure wound therapy as commercialized by the Assignee or its parent.

This aspect of the present invention generally comprises a pad for insertion substantially into the wound site and a wound drape for sealing enclosure of the pad at the wound site. In some embodiments, wherein the pad comprises a foam, the pad has relatively few open foam cells in contact with the areas where epithelial cell growth is to be encouraged so as to avoid unwanted adhesions, but having sufficiently numerous open foam cells so that drainage and V.A.C.® therapy may continue unimpaired. The pad is placed in fluid communication with a vacuum source for promotion of fluid drainage, as is known in the art. In some embodiments the pad may comprise bioabsorbable polymers. In some embodiments the pad may have embedded in that side to be applied to the wound, a cell growth lattice, matrix, or scaffolding, which may be bioabsorbable, all of which have been used in the art to describe similar constructs, and that are noninvasive to the known V.A.C.® therapy, thereby requiring no modification thereof.

Wherein the pad of the present invention is provided with a bioabsorbable, or includable, fibrous growth-enhancing matrix, numerous suitable materials for this purpose are known to the art. Such suitable materials include collagen, dissolvable nylon, soluble plastics, and fibrous ceramic material. An exemplary fibrous ceramic material that may be utilized is an ultra-low density fused-fibrous ceramic manufactured by Materials Evolution and Development USA, Inc., under the trade name P.R.I.M.M™ (Polymeric Rigid Inorganic Matrix Material), and further described in U.S. Pat. No. 5,951,295, issued to Lyles, et al., which is incorporated herein by reference. Additional materials may include alginates, fibrin gels, fused fibers and other similar materials utilized by those skilled in the art, that are capable of providing an invadable space and scaffolding for cellular growth. The fibrous growth-enhancing matrices of the present invention also encompass acellular dermal matrix preparations, such as AlloDerm (Lifecell), Oasis (Cook) and Integra® (Johnson & Johnson). AlloDerm is fabricated from cadaveric skin such as to produce an acellular dermis that is free of the cells responsible for the antigenic response to allograft skin. After processing, the skin is reduced to a basement membrane and properly oriented dermal collagen matrix. Oasis is a sterile acellular graft material extracted from the small intestine of pigs. Integra is composed of bovine and shark cartilage glycosaminoglycans. Alternatively, the growth-enhancing matrix may be non-fibrous, such as a gel-like growth-enhancing matrix. This matrix comprises a cell growth enhancing substrate that is up to over 90% open space. The fibers, or other particles, and spaces create nooks and crannies that provide an excellent environment to enhance cell growth, and thereby facilitate the vacuum induced healing process.

Upon placement of the pad, an airtight seal is formed over the wound site to prevent vacuum leakage. In use the V.A.C.® therapy is conducted as known and, if desired, in some embodiments cell growth enhancement therapy is added by simply placing the matrix on the pad that is located within the wound. Given the addition of a suitable surface to which the fibrous lattice may be attached, the cell growth is channeled into the most desirable form and location, but is kept away from the pad itself. In some embodiments, utilization of bioabsorbable branched polymers in the pad itself, in addition to, or in place of the cell growth enhancing matrix, can allow the pad to remain in place during the healing process. As cell growth continues, the pad is absorbed, and there is no need to remove the pad.

Some embodiments comprise use of bioabsorbable branched polymers within a layer of the pad adjacent the wound, such that upon removal of the pad during dressing changes, the bioabsorbably branched polymer layer is left behind, leaving the wound site itself undisturbed. Additionally, the cell growth enhancing substrate matrix may be incorporated within the polymer layer to further enhance cellular growth at the wound site.

Figure 26:
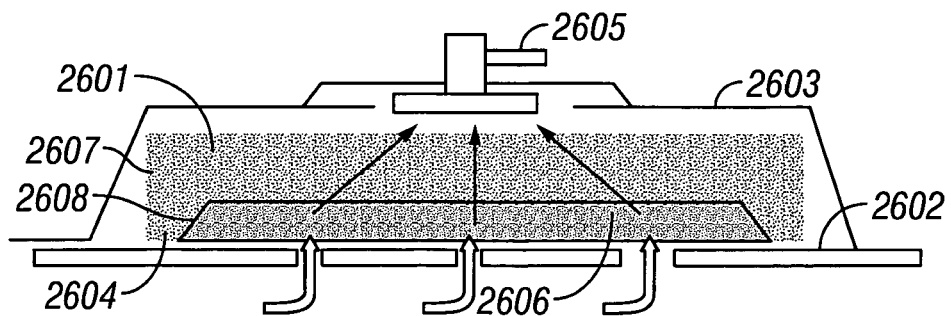
FIG. 26 shows, in partial cutaway perspective view, an embodiment of the fourth aspect of the present invention incorporating negative pressure therapy, as applied to a wound site.
Figure 27:
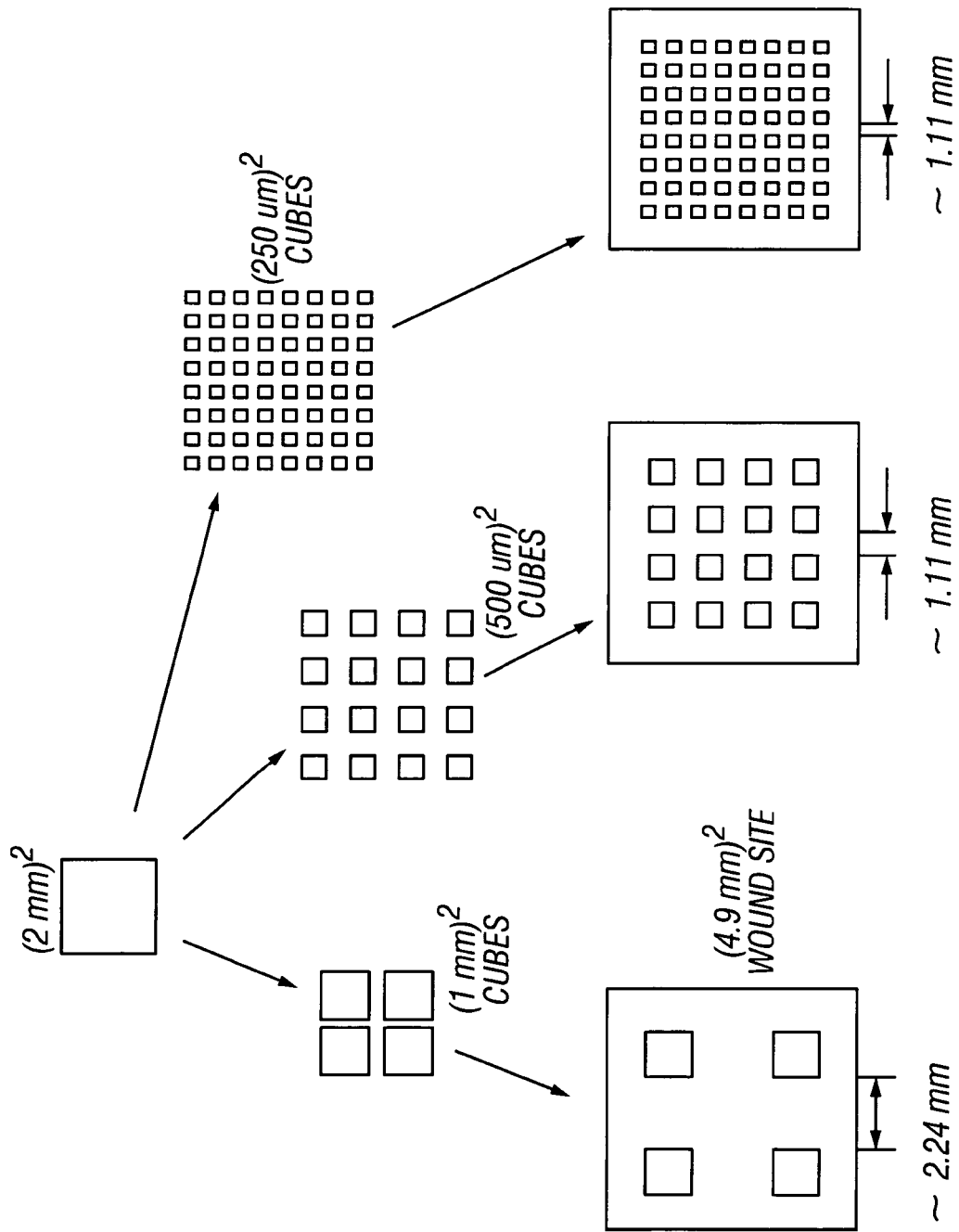
FIG. 27 depicts a schematic of skin piece cube size and its relationship to spacing. "A" shows a split-thickness skin graft harvest site that is 2 mm on a side. "B" demonstrates how dividing the original harvest into smaller and smaller cubes leads to greater numbers of cubes for a given area of harvest. "C" shows that a 6:1 expansion ratio allows a 2 mm×2 mm harvest to cover a 4.9 mm×4.9 mm wound site. The spacing for a completely homogeneous dispersion of each of three different cube sizes is indicated beneath each square.

Referring now to FIG. 26, an exemplified embodiment of this aspect of present invention is shown to generally comprise a foam pad 2601 for insertion substantially into the wound site 2602 and a wound drape 2603 for sealing enclosure of the foam pad 2601 at the wound site 2602. According to this embodiment, the foam pad 2601 is modified to contain a cell growth-enhancing matrix, or lattice 2604, whereby a desired highly porous cell growth enhancing substrate may be directed into and about the wound site 2602. After insertion into the wound site 2602 and sealing with the wound drape 2603, the foam pad 2601 is placed in fluid communication with a vacuum source for promotion of fluid drainage, as known to those of ordinary skill in the art.

With the exception of those modifications to the foam pad 2601 detailed further herein, the foam pad 2601, wound drape 2603 and vacuum source are detailed in WO9605873, which is hereby incorporated as though fully set forth herein. As detailed in WO9605873, the foam pad 2601 preferably comprises a highly reticulated, open-cell polyurethane or polyether foam for suitable permeability of wound fluids while under suction. Embodiments include foams having at least 90% and at least 95% of interconnecting cells. As also detailed in WO9605873, the foam pad 2601 is preferably placed in fluid communication, via a plastic or like material hose 2605, with a vacuum source, which preferably comprises a canister safely placed under vacuum through fluid communication, via an interposed hydrophobic membrane filter, with a vacuum pump. The filter protects the vacuum pump from contamination by wound drainage fluids sucked into the canister. Finally, WO9605873 also details the wound drape 2603, which in some embodiments comprises an elastomeric material at least peripherally covered with a pressure sensitive adhesive, such as an acrylic adhesive, for sealing application over the wound site 2602. An elastomeric wound drape accommodates changes in pressure in the wound area during intermittent operation of the vacuum pump.

Those components as are described in WO9605873 are generally employed as known in the art with the exception that the foam pad 2601 is provided with a matrix 2604. This matrix 2604 is shown to comprise porous material 2606 that has been formed into a plurality of sections 2607. The material 2606 is implanted in the foam pad 2601 at the base 2608 of the pad 2601. Because it is necessary to trim the foam pad 2601 in preparation for V.A.C.® therapy wound treatment, material 2606 preferably is placed in the central portion of pad 2601. Applicant does not intend to limit itself to a regular or symmetrical arrangement of material 2606 or sections by use of the term "matrix".

In some embodiments, the pad itself comprises, consists essentially of, or consists of bioabsorbable branched polymers (not shown in FIG. 26), wherein such pads may be utilized alone or in combination with the matrix 2604.

Upon placement of the pad 2601, having the matrix 2604 embedded therein, and/or protruding therefrom, and/or comprised of bioabsorbable branched polymers, the wound drape 2603 is applied over the pad to form an airtight seal over the wound site. In use, the V.A.C.® therapy is conducted as known and, if desired, cell growth enhancement therapy is added by simply providing the matrix 2604 comprising material 2606. In this manner, cell growth enhancement therapy may be conveniently combined with existing V.A.C.® therapies, without loss of V.A.C.® therapy performance and without inconvenience or overly increased cost.

Embodiments of this aspect of the invention also provide for the use of negative pressure therapy in combination with the use of skin micrograft particles, which may be nanograft particles. In this regard, micrograft particles may be applied to the skin, optionally in a gel, and a primary dressing is applied over the micrograft particles and can be fastened to the skin peripheral to the wound. Suitable dressings include non-adherent dressings, including, but not limited to, Telfa Clear (Kendall), Acticoat 7 (Smith & Nephew) and Tegapore™ (3M). The gel may be an antibacterial gel as are known in the art, such as Bacitracin, or a gel growth-enhancing matrix as disclosed supra. Micrograft particles may also be deposited on or incorporated in a bioabsorbable material or a fibrous growth-enhancing matrix. In some embodiment, a fibrous growth enhancing matrix, which may be an acellular dermis is applied to a wound site, micrograft particles are deposited on the surface of the acellular dermis, and negative pressure therapy is applied. In some embodiments a primary dressing is applied to the micrograft particles prior to application of a negative pressure therapy pad. In alternative embodiments, micrograft particles and a supporting growth-enhancing matrix, which may be a acellular dermis, are incorporated into a negative pressure therapy pad prior to application to a wound site. In some embodiments, the pad also comprises a primary layer between the pad and the micrograft particles, which may be a non-adherent dressing. Embodiments comprising the application of the pad with micrograft particles and an acellular dermis, provide a one-step treatment for both dermal replacement and epithelialization. Negative pressure therapy may also be used at the wound site prior to the application of micrograft particles to the wound site.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Aggregation of Nanografts on a Wound Site when Distributed by Mechanical Spreading STSG harvesting and wound preparation were performed on anesthetized pigs. STSGs were harvested using a commercially available Padgett Dermatome at a nominal depth setting of 0.013 inch (335 µm). They were subsequently minced to 600 µm nanograft particles using a skin mincing device wherein the operation was performed in 2 steps, or cuts. The first cut produced strips of tissue parallel to each other. These strips were then rotated 90 degrees and cut a second time with the parallel blade mincing device to produce cubes from the STSG.

Figure 28:
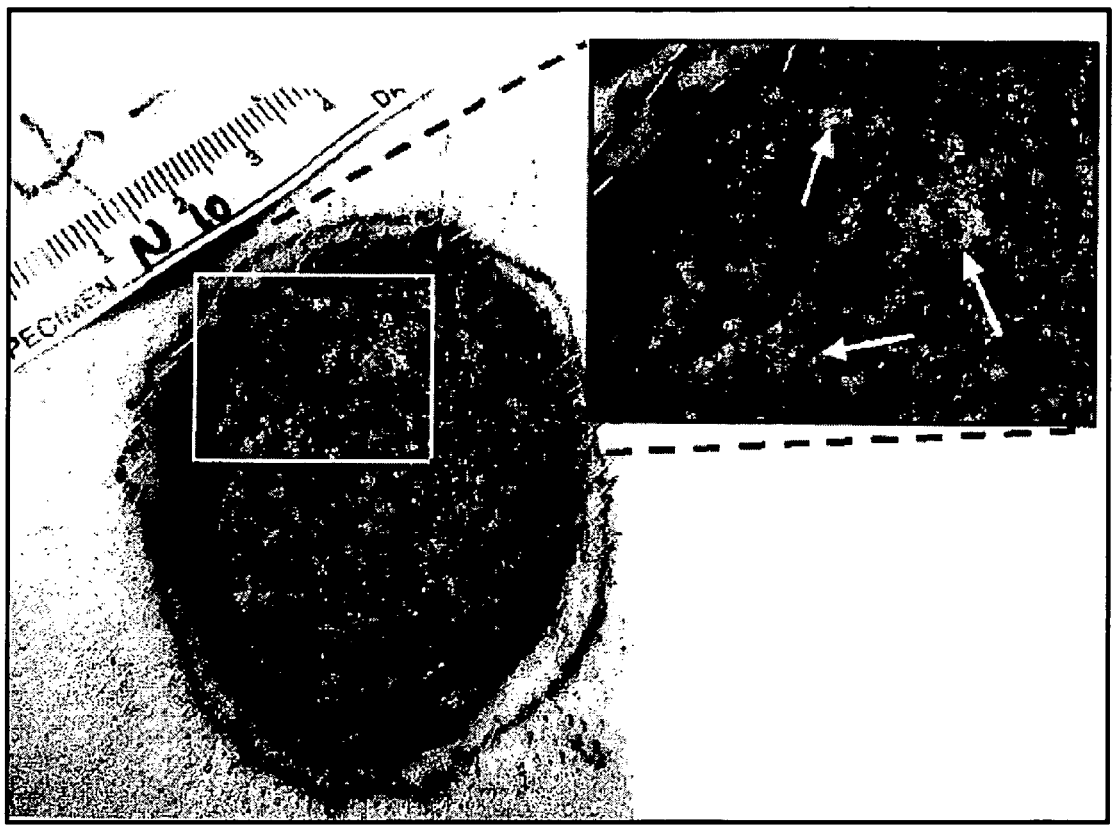
FIG. 28 shows a photograph of mechanical spreading of nanograft particles on a wound site. Arrows in inset image indicate clumping of nanograft particles.

The nanografts were mechanically spread onto a wound site at an expansion ratio of 6:1. As shown in FIG. 28, the mechanical spreading results in clumps of skin particles that are interspersed with areas that have little or no coverage by the nanografts. Characteristic clumps are exemplified in the inset image as indicated by the arrows.

Example 2

Vacuum Assisted Dispersion of Nanografts onto a Nylon Mesh

STSG harvesting was performed on anesthetized pigs. STSGs were harvested using a commercially available Padgett Dermatome at a nominal depth setting of 0.013 inch (335 µm). They were subsequently minced to 600 µm nanograft particles using a skin mincing device wherein the operation was performed in 2 steps, or cuts. The first cut produced strips of tissue parallel to each other. These strips were then rotated 90 degrees and cut a second time with the parallel blade mincing device to produce cubes from the STSG. The nanografts were stained purple with crystal violet for ease of viewing and suspended in saline.

Figure 29:
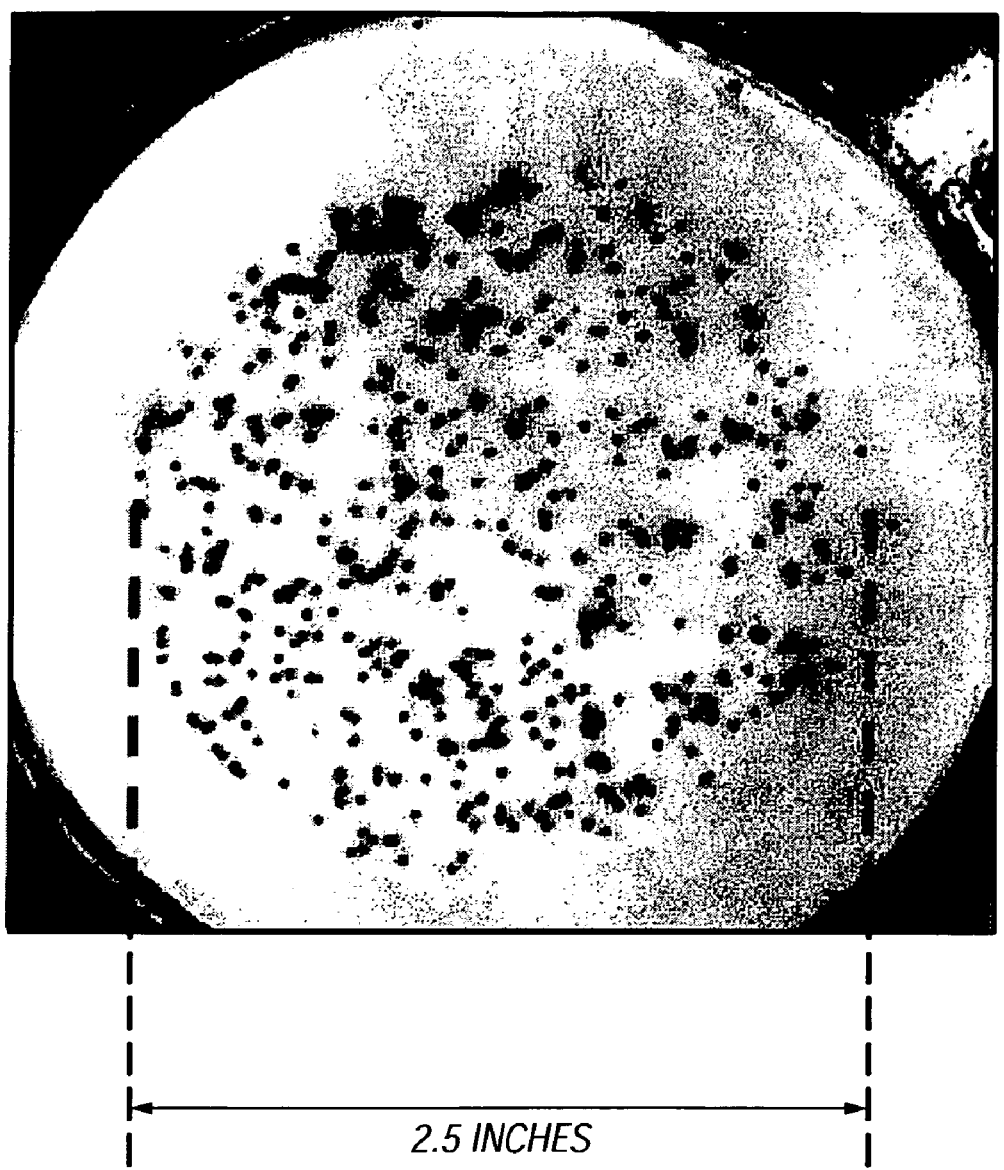
FIG. 29 shows a photograph of deposition of nanograft particles stained with crystal violet onto a nylon mesh resulting from a vacuum being applied to a saline suspension of nanograft particles. The dispersion pattern is significantly more even than that observed with mechanical spreading.

A nylon mesh was placed into a vacuum reservoir and a particle restraint device was inserted to confine settlement of particles to an area of diameter of 2.5 inches (same diameter as test wound in Example 3). The suspension of nanografts was placed into the interior of the restraint device and vacuum was applied. The deposition of the nanografts on the nylon mesh is shown in FIG. 29. This method obviated the clumps observed with mechanical spreading and resulted in a significantly more even dispersion of the nanografts. Wherein the nanografts were not stained with crystal violet, the nylon mesh with nanografts so deposited is suitable for application to a wound site.

Example 3

Effect of Nanograft Size on Outgrowth Materials & Methods

STSG harvesting and mincing for this study were performed on live, anaesthetized pigs with visual proliferation studies starting ~24 hours after harvest. Minced STSG specimens were plated in 6-well (35 mm diameter) collagen coated plates (biocoat, Becton Dickinson) at expansion ratios of ~6:1. STSGs were harvested using a commercially available Padgett Dermatome at a nominal depth setting of 0.014 inch (355 μm). They were subsequently minced to 300 μm×300 μm, 600 μm×600 μm and 1000 μm×1000 μm squares using a skin mincing device wherein the operation was performed in 2 steps, or cuts. The first cut produced strips of tissue parallel to each other. These strips were then rotated 90 degrees and cut a second time with the parallel blade mincing device to produce cubes of STSG of various dimensions. The spacing between the blades was varied to vary the size of the cubes.

In the time between harvest and plating, samples were maintained in supplemented Waymouth's medium. The Waymouth's medium (MB 752/1, Gibco) was supplemented with 0.38 mg/ml L-arginine, 0.38 mg/ml sodium pyruvate, 1.9 μg/ml putrescine, 8 μg/ml insulin, 8 ug/ml hydrocortisone, $10^{-10}$ M cholera toxin, 100 μ/ml penicillin, 100 μg/ml streptomycin. Culturing was performed in complete Waymouth's medium, which was identical to supplemented Waymouth's medium and only differed in that 15% fetal bovine serum was added. During culture, Waymouth's medium was changed every 3 days.

Visual proliferation was measured as follows. Minced skin was plated in 6-well, collagen coated culture plates (biocoat, Becton Dickinson) at a 6:1 expansion ratio in low suspension volumes. Low suspension volumes were used to aid the attachment of particulates to the bottom of the dishes. Additionally, long attachment times of 48 hours were used in order to allow maximum attachment with the least disturbance possible. After 48 hours, dishes were topped up to ~10 ml with Waymouth's containing 15% FBS and the medium was changed every 3 days.

Specimens were fixed at 5 days and 12 days with 10% buffered formalin solution (pH 7.4) for 2-24 hours. In many cases, the quantity of tissue minced was not enough to perform both a 5 day and 12 day culture experiment. In these cases, only the 12 day experiment was performed. After fixation, cells were washed with PBS, stained using crystal violet and digitally imaged using a Nikon Coolpix 885 digital camera. Images for quantitative measurement were first imported into Adobe Photoshop, where they were cropped to include only the surface area of the culture well bottom. These cropped images were then imported into SigmascanPro and digitally analyzed to determine the percent of the culture plate covered by the cubes, as well as, the keratinocytes and fibroblast outgrowth from the cubes. Sigmascan was normalized to a size standard by using the diameter of the culture well as a reference (diameter=35 mm).

For each animal, the three cube sizes were compared to each other at Day 12. Analysis of data from the first 6 sets of valid in vitro specimens provided sufficient data to meet the objectives of this study. One-way ANOVA was used to compare the outgrowth coverage seen in the three cube sizes per animal. With the achievement of a positive result, the three cube sizes were studied using a t-test multiple comparison method to determine which cube size led to the most outgrowth. A small amount of variability was inherent in the measurement method that allowed an occasional outgrowth value that was greater than 100%, though none of them ever exceeded 102.5%. When this happened, the value was taken to be 100% for the statistical analysis. Finally, the data points for all 6 animals were pooled together for each cube size and then analyzed for differences in outgrowth between them.

Results

Outgrowth of was quantified using digital photography and the results are summarized in Table 1. Outgrowth was present in every cube size with the 300 μm nanograft showing the least outgrowth coverage of all. Outgrowth from this cube size was statistically less in every case than that seen in either the 600 μm nanograft, or the 1000 μm nanograft. The 600 μm nanograft showed the most robust outgrowth and proliferation at day 12 under these culture conditions. The data from 6 animals were pooled and analyzed statistically demonstrating that outgrowth coverage from the 600 μm nanograft was greater than both the 300 μm nanograft (p<0.0001) and 1000 μm nanograft (p~0.055).

TABLE 1

|  | % Coverage | | |
| --- | --- | --- | --- |
|  | 300 μm nanografts | 600 μm nanografts | 1000 μm nanografts |
| Subject 1 | 34.9 ± 6.4% | 76.2 ± 8.9% | 64.8 ± 8.7% |
| Subject 2 | 76.5 ± 8.3% | 89.7 ± 4.1% | 70.0 ± 23.1% |
| Subject 3 | 57.9 ± 4.1% | 99.1 ± 0.6% | 95.9 ± 5.7% |
| Subject 4 | 51.1 ± 8.1% | 97.4 ± 2.6% | 96.0 ± 1.7% |
| Subject 5 | 75.1 ± 8.6% | 90.9 ± 3.9% | 83.0 ± 9.8% |
| Subject 6 | 39.7 ± 8.6% | 69.1 ± 14.6% | 72.6 ± 10.9% |
| Average | 55.4 ± 17.6% (n = 34) | 87.4 ± 13.0% (n = 35) | 80.6 ± 16.2% (n = 35) |

Overall, the 600 μm nanografts provided the most robust cellular outgrowth and achieved the greatest outgrowth coverage of the 3 sizes studied.

Example 4

Negative Pressure Therapy Foam Pad

The open celled foam previously described in section D of the Detailed Description is formed into a pad. The general principles set forth in U.S. Pat. No. 5,795,584, issued to Totakura et al., at Col. 4 line 64-Col. 5 line 42, are followed to create a structure superimposed on the bottom of the pad. Holes are placed in those portions of the non-bioabsorbable substrate relatively remote from the bioabsorbable cell growth enhancing matrix substrate. The matrix covers a portion of the pad located within the boundaries of the wound being treated. The pad is then completely covered by an airtight drape, and subjected to sub atmospheric pressure, as is the standard practice for utilizing V.A.C.® therapy. The matrix is absorbed within the expected useful life of the pad, so, that when the pad is removed, the matrix had been absorbed, and the growing cells are not disturbed. The pad is replaced, if necessary, either by a conventional pad or by a matrix containing pad, as deemed therapeutically necessary.

Example 5

Negative Pressure Therapy Pad

A conventional pad is selected. A collagen cell growth matrix is applied to a portion of the bottom thereof The general principles of V.A.C.® therapy are followed, with the matrix containing pad substituted for a conventional pad. During the expected duty cycle of the pad, the collagen matrix is absorbed by the growing cells, so that when the pad is removed, the matrix had been absorbed, and the growing cells are not disturbed. The pad is replaced, if necessary, either by a conventional pad or by a matrix containing pad, as deemed therapeutically necessary.

Example 6

Negative Pressure Therapy Pad

The procedure set forth in Example 5 is followed. However an ultra-low density fused-fibrous ceramic, sometimes referred to under the trademark P.R.I.M.M., is substituted for the collagen matrix thereof. The general principles of V.A.C.® therapy are followed. During the expected duty cycle of the pad, the ultra-low density fused fibrous ceramic is absorbed by the growing cells, so, that when the pad is removed, the ultra-low density fused-fibrous ceramic had been absorbed, and the growing cells were not disturbed. The pad is replaced, if necessary, either by a conventional pad or by a matrix containing pad, as deemed therapeutically necessary.

Example 7

Negative Pressure Therapy Pad

Many suitable bioabsorbable materials have been used for sutures, surgical implements, and the like. Examples of such materials are set forth in the following U.S. patents, to wit: U.S. Pat. No. 5,997,568, issued to Liu and the following patents issued to Roby et al: U.S. Pat. Nos. 5,914,387; 5,902, 874 and 5,902,875. A matrix comprising one or more of these, or similar materials, are placed upon a conventional pad. The general principles of V.A.C.® therapy are followed. During the expected duty cycle of the pad, the bioabsorbable material is absorbed by the growing cells, so, that when the pad is removed, the bioabsorbable material had been absorbed, and the growing cells were not disturbed. The pad is replaced, if necessary, either by a conventional pad or by a matrix containing pad, as deemed therapeutically necessary.

Example 8

Negative Pressure Therapy Pad

A bioabsorbable branched polymer, similar to that described in U.S. Pat. No. 5,578,662 issued to Bennet et al., forms the pad. The general principles of V.A.C.® therapy are followed with the bioabsorbable branched polymer pad substituted for the conventional pad. During the expected duty cycle of the pad, the pad is absorbed by the growing cells, so that there is no need to replace the pad and disturb the wound site. If further treatment is deemed necessary, a conventional pad, or an additional matrix containing pad, or an additional bioabsorbable branched polymer pad may be placed in the wound site, and V.A.C.® therapy continued.

All of the methods and apparatus disclosed and claimed herein can be made and executed without undue experimentation in light of the present disclosure. While the compositions and methods of this invention have been described in terms of preferred embodiments, it will be apparent to those of skill in the art that variations may be applied to the methods and apparatus and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A skin-harvesting device, comprising:
 a base, comprising a base plate with side rails, a proximal end, a distal end, two side ends and defining a window adjacent to the proximal end, and adapted during use to be pressed against a harvest site; and
 a cutting frame, comprising a frame base configured to slide in the side rails, a blade housing adapted to house a blade at a predetermined angle therein, wherein said blade is aligned traverse to the side ends and generally parallel to the proximal end and wherein the predetermined angle of the blade relative to the proximal end forms an oblique angle, and an adjustable thickness plate coupled to the cutting frame and adapted to raise or lower to vary thickness of any material cut by the blade, wherein the window is configured to allow a user to see a harvest site during use.

2. The skin-harvesting device of claim 1, further comprising a motor having an axle coupled through the cutting frame to the blade and adapted to oscillate the blade.

3. The skin-harvesting device of claim 2, further comprising a power source connected to the motor.

4. The skin-harvesting device of claim 3, wherein the power source comprises a battery pack connected to the motor.

5. The skin-harvesting device of claim 2, further comprising an ergonomic cover housing the cutting frame and motor, the ergonomic cover defining a skin-graft retrieval area to allow during use access to skin collected after harvesting.

6. The skin-harvesting device of claim 1, wherein the side rails are internal slide rails formed at the side ends of the base and further comprising track fixtures positioned on lateral ends of the cutting frame, the track fixtures being adapted to slide in the slide rails of the base and thereby translate the cutting frame along the base.

7. The skin-harvesting device of claim 1, wherein the side rails are external slide rails formed at side ends of the base and further comprising track fixtures positioned on lateral ends of the cutting frame, the track fixtures being adapted to slide in the external slide rails of the base and thereby translate the cutting frame along the base.

8. The skin-harvesting device of claim 1, wherein the base has an open end to allow the cutting frame to be removed from or placed within the base.

9. The skin-harvesting device of claim 1, wherein the blade is coupled to the blade housing via thermoplastic welding or via fasteners.

10. The skin-harvesting device of claim 1, further comprising tab portions positioned along the proximal end of the base adjacent the window to provide a user with an area to apply pressure to the base during use of the device.

11. The skin-harvesting device of claim 1, further comprising grips positioned on the base adapted to allow a user an area to apply pressure to the base during use of the device.

12. The skin-harvesting device of claim 1, further comprising grips positioned on the cover adapted to provide a user an area to grip the cover to translate the cover within the base during use of the device.

13. The skin-harvesting device of claim 1, further comprising a plurality of ridges formed on the skin-facing surface of the adjustable thickness plate, the plurality of ridges being adapted to during use grip the skin prior to incision.

14. The skin-harvesting device of claim 1, wherein the base further comprises a plurality of ridges formed on the skin-facing surface of the base adjacent the window adapted during use to grip the skin adjacent the base window.

15. The skin-harvesting device of claim 1, further comprising at least one fastener coupled through the cutting frame to the adjustable depth plate adapted to raise and lower the adjustable depth plate.

16. The skin-harvesting device of claim 1, further comprising a skin-depth wheel or a skin-depth slide positioned on the cover and coupled to the adjustable thickness plate to raise or lower the adjustable thickness plate with respect to the skin during use.

17. The skin-harvesting device of claim 16, further comprising indicia printed on the cover adjacent the skin-depth wheel or skin-depth slide to indicate the depth of the adjustable thickness plate when the skin-depth wheel is rotated or the skin-depth slide is moved.

18. The skin-harvesting device of claim 1, further comprising a roller wheel positioned before the blade and blade holder and rotating about an axle coupled to the cover, wherein said roller wheel comprises a plurality of teeth about the perimeter of the wheel adapted during use to puncture or hook the skin prior to incision by the blade adapted to secure the skin onto the roller wheel after severance.

19. A device for collecting tissue for skin-grafting, comprising a base plate defining a base window at a forward end thereof and having slide rails positioned at lateral internal edges of the base plate;

a frame base adapted to slide in the slide rails of the base plate;
a frame connected to the frame base;
a plurality of slides coupled along lateral edges of the frame and adapted to engage the slide rails and slide freely therethrough;
base grips positioned along lateral ends of the base plate and adapted to support pressure during use from a user thereon;
an ergonomic cover adapted to encompass the frame and frame base and defining a cover window at a forward end thereof;
cover grips positioned at lateral edges of the cover adapted to allow during use a user to firmly grip the cover and apply pressure thereon during use of the device;
a motor coupled to the frame; a power source connected to the motor;
a blade holder coupled to a forward section of the frame via a guide pin;
a blade coupled to the blade holder at a predetermined angle;
an adjustable depth plate coupled to the frame adjacent and forward from the blade holder; and
a cam connected to the adjustable depth plate having a cam dial adapted to control the raising and lowering of the adjustable depth plate with respect to the base window, wherein the cover window is configured to allow a user to see skin harvested from the harvest site.

20. A method of harvesting skin comprising: contacting a skin harvest site with the skin-harvesting device of claim 1; applying pressure to the base of the skin-harvesting device such that skin from the harvest site protrudes through the window in the base plate of said harvesting device; adjusting the adjustable thickness plate of the harvesting device to press the skin protruding through the window to form a uniform surface substantially parallel to the base; and harvesting the a split-thickness skin sample by translating the cutting frame along the base of the harvesting device.

21. A method of collecting skin for a skin-graft, comprising:
pressing the device of claim 19 against a skin donor such that a uniform surface of donor skin protrudes substantially parallel to the base through the base window;
pressing the adjustable depth plate against the donor skin such that the protruding donor skin is of uniform thickness; and
sliding the frame coupled to the blade holder along the base so as to sever the protruding donor skin.

* * * * *

UNITED STATES PATENT AND TRADEMARK OFFICE
CERTIFICATE OF CORRECTION

| | | |
|---|---|---|
| PATENT NO. | : 7,666,192 B2 | Page 1 of 1 |
| APPLICATION NO. | : 11/093740 | |
| DATED | : February 23, 2010 | |
| INVENTOR(S) | : Seegert et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 919 days.

Signed and Sealed this
Eleventh Day of January, 2011

David J. Kappos
*Director of the United States Patent and Trademark Office*